US008110709B2

(12) United States Patent
Papp et al.

(10) Patent No.: US 8,110,709 B2
(45) Date of Patent: Feb. 7, 2012

(54) STABILIZATION OF HYDROFORMYLATION CATALYSTS BASED ON PHOSPHORAMIDE LIGANDS

(75) Inventors: Rainer Papp, Speyer (DE); Wolfgang Ahlers, Worms (DE); Thomas Mackewitz, Römerberg (DE); Rocco Paciello, Bad Dürkheim (DE); Martin Volland, Heidelberg (DE)

(73) Assignee: BASF SE, Ludwigshafen (DE)

( * ) Notice: Subject to any disclaimer, the term of this patent is extended or adjusted under 35 U.S.C. 154(b) by 198 days.

(21) Appl. No.: 10/576,282

(22) PCT Filed: Oct. 22, 2004

(86) PCT No.: PCT/EP2004/011986
§ 371 (c)(1),
(2), (4) Date: Apr. 19, 2006

(87) PCT Pub. No.: WO2005/039762
PCT Pub. Date: May 6, 2005

(65) Prior Publication Data
US 2006/0224000 A1 Oct. 5, 2006

(30) Foreign Application Priority Data
Oct. 23, 2003 (DE) .................... 103 49 343

(51) Int. Cl.
C07C 45/50 (2006.01)
C07F 9/572 (2006.01)
C07F 9/06 (2006.01)
(52) U.S. Cl. .......... 568/454; 568/451; 548/412; 564/12; 564/14
(58) Field of Classification Search .......... 564/14, 564/12; 548/412; 568/451, 454
See application file for complete search history.

(56) References Cited

U.S. PATENT DOCUMENTS

| | | | |
|---|---|---|---|
| 4,260,828 A * | 4/1981 | Morrell et al. ................ 568/454 |
| 4,283,562 A * | 8/1981 | Billig et al. .................. 568/454 |
| 4,567,306 A | 1/1986 | Dennis et al. | |
| 4,599,206 A | 7/1986 | Billig et al. | |
| 4,654,445 A | 3/1987 | Ono et al. | |
| 4,717,775 A | 1/1988 | Billig et al. | |
| 4,774,361 A | 9/1988 | Maher et al. | |
| 5,710,344 A | 1/1998 | Breikss et al. | |
| 5,731,472 A * | 3/1998 | Leung et al. ................ 568/454 |
| 5,741,942 A | 4/1998 | Bryant et al. | |
| 5,741,943 A | 4/1998 | Bryant et al. | |
| 5,741,944 A | 4/1998 | Bryant et al. | |
| 5,741,945 A | 4/1998 | Bryant et al. | |
| 5,744,649 A | 4/1998 | Bryant et al. | |
| 5,763,670 A | 6/1998 | Billig et al. | |
| 5,763,671 A | 6/1998 | Bryant et al. | |
| 5,763,677 A | 6/1998 | Bryant et al. | |
| 5,763,680 A | 6/1998 | Bryant et al. | |
| 5,767,321 A | 6/1998 | Billig et al. | |
| 5,786,517 A | 7/1998 | Bryant et al. | |
| 5,789,625 A | 8/1998 | Bryant et al. | |
| 5,874,640 A | 2/1999 | Bryant et al. | |
| 5,886,235 A | 3/1999 | Bryant et al. | |
| 5,892,119 A | 4/1999 | Bryant et al. | |
| 5,917,095 A | 6/1999 | Bryant et al. | |
| 6,018,081 A | 1/2000 | Burke et al. | |
| 6,229,052 B1 * | 5/2001 | Bunel et al. ................ 568/454 |
| 7,173,138 B2 * | 2/2007 | Ahlers et al. ................ 548/101 |
| 2005/0059841 A1 | 3/2005 | Drent et al. | |

FOREIGN PATENT DOCUMENTS

| | | |
|---|---|---|
| DE | 10206697 | 8/2002 |
| DE | 10256164 | 6/2003 |
| DE | 10342760 A1 | 3/2004 |
| EP | 0183199 | 6/1986 |
| EP | 0149894 | 3/1989 |
| EP | 0276231 | 10/1991 |
| EP | 0214622 | 5/1992 |
| EP | 0155508 | 12/1992 |
| WO | WO-97/20794 | 6/1997 |
| WO | WO-97/20795 | 6/1997 |
| WO | WO-97/20796 | 6/1997 |
| WO | WO-97/20797 | 6/1997 |
| WO | WO-97/20798 | 6/1997 |
| WO | WO-97/20799 | 6/1997 |
| WO | WO-97/20800 | 6/1997 |
| WO | WO-97/33854 | 9/1997 |
| WO | WO-00/56451 | 9/2000 |
| WO | WO-02/083695 | 10/2002 |
| WO | WO-03/018192 | 3/2003 |
| WO | WO-03/070679 | 8/2003 |
| WO | WO-2004/078766 | 9/2004 |

OTHER PUBLICATIONS

Oxford Dictionary of Biochemistry and Molecular Biology Rev. Ed., Smith, A.D., 1997, Oxford University Press, p. 504.*
Organic Chemistry, 4th Ed., McMurry, J., Brooks/Cole Publishing Co., p. 1161.*
Phosphorus an Outline of its Chemistry, Biochemistry and Uses, Fifth Ed. Corbridge, D.E.C. Elsevier, p. 407.*
Jackstell et al. Eur. J. Org. Chem. 2001, 3871-3877.* van Leeuwen in Chapter 9 of Catalysis by Metal Complexes, vol. 22, Rhodium Catalyzed Hydroformylation, 2002, Kluwer Acad. Pub., pp. 233-251.*
Moloy et al. J. Am. Chem. Soc. 1995, 117, 7696-7710.*
Xu et al. Tetrahedron Lett. 1997, 38(42), 7337-7340.*
Anna M. Trzeciak et al., "Novel rhodium complexes with N-pyrrolylphosphines: attractive precursors of hydroformylation catalysts", J. Chem. Soc., Dalton Trans., 1997, pp. 1831-1837.
International Search Report No. PCT/EP2004/011986, dated Dec. 22, 2004, 8 pages.

* cited by examiner

Primary Examiner — Jason M Nolan
(74) Attorney, Agent, or Firm — Connolly Bove Lodge & Hutz LLP

(57) ABSTRACT

The present invention relates to a process for the hydroformylation of ethylenically unsaturated compounds by reaction with carbon monoxide and hydrogen in the presence of a catalytically active fluid which comprises a dissolved metal complex of a metal of transition group VIII of the Periodic Table of the Elements with at least one phosphoramidite compound as ligand, wherein the fluid is brought into contact with a base.

20 Claims, 1 Drawing Sheet

STABILIZATION OF HYDROFORMYLATION CATALYSTS BASED ON PHOSPHORAMIDE LIGANDS

CROSS REFERENCE TO RELATED APPLICATION

The present application is a National Stage application of PCT/EP2004/011886, filed Oct. 22, 2004, which claims priority from German Patent Application No. DE 103 49 343.3, filed Oct. 23, 2003.

DESCRIPTION

The present invention relates to a process for the hydroformylation of ethylenically unsaturated compounds by reaction with carbon monoxide and hydrogen in the presence of a catalytically active fluid which comprises a dissolved metal complex of a metal of transition group VIII of the Periodic Table of the Elements with at least one phosphoramidite compound as ligand, wherein the fluid is brought into contact with a base.

Hydroformylation or the oxo process is an important industrial process and is employed for preparing aldehydes from olefins, carbon monoxide and hydrogen. These aldehydes can, if desired, be hydrogenated by means of hydrogen in the same process to give the corresponding oxo alcohols. The reaction itself is strongly exothermic and generally proceeds under superatmospheric pressure and at elevated temperatures in the presence of catalysts. Catalysts used are Co, Rh, Ir, Ru, Pd or Pt compounds or complexes which may be modified by means of N- or P-containing ligands to influence the activity and/or selectivity. In the hydroformylation reaction of olefins having more than two carbon atoms, the formation of mixtures of isomeric aldehydes can occur due to the possible CO addition onto each of the two carbon atoms of a double bond. In addition, double bond isomerization, i.e. a shift of internal double bonds to a terminal position and vice versa, can also occur when using olefins having at least four carbon atoms.

Owing to the significantly greater industrial importance of α-aldehydes, optimization of the hydroformylation catalysts to achieve a very high hydroformylation activity and at the same time a very low tendency to form olefins having double bonds which are not in the α position is desirable. In addition, there is a need for hydroformylation catalysts which lead to good yields of α- and in particular n-aldehydes even when linear internal olefins are used as starting materials. Here, the catalyst has to make possible both the establishment of an equilibrium between internal and terminal double bond isomers and the very selective hydroformylation of the terminal olefins.

WO 00/56451 describes hydroformylation catalysts based on phosphinamidite ligands in which the phosphorus atom together with an oxygen atom to which it is bound forms a 5- to 8-membered heterocycle.

WO 02/083695 describes chelating pnicogen compounds in which at least one pyrrole group is bound via the pyrrole nitrogen to each of pnicogen atoms. These chelating pnicogen compounds are suitable as ligands for hydroformylation catalysts.

WO 03/018192 describes, inter alia, pyrrole-phosphorus compounds in which at least one pyrrole group which is substituted and/or integrated into a fused ring system is covalently bound via its pyrrole nitrogen to the phosphorus atom, which display a very good stability when used as ligands in hydroformylation catalysts.

The German patent application 102 43 138.8, which is not a prior publication, describes pnicogen compounds which have two pnicogen atoms and in which pyrrole groups can be bound via a pyrrole nitrogen to both pnicogen atoms and both pnicogen atoms are bound via a methylene group to a bridging group. These pnicogen compounds are suitable as ligands for hydroformylation catalysts.

The abovementioned catalysts display a high regioselectivity to terminal product aldehydes both in the hydroformylation of α-olefins and in the hydroformylation of internal linear olefins. In addition, they have a good stability under the hydroformylation conditions, particularly in the case of hydroformylation catalysts based on ligands in which one or more 3-alkylindole group(s) is/are bound to the phosphorus atom. Nevertheless, additional stabilization is desirable with a view to the long catalyst lives required for large-scale industrial use.

DE-A-102 06 697 describes a hydroformylation process which makes it possible for the products of value to be separated off and the catalyst to be recirculated with a very low loss of activity. This is achieved using a hydroformylation catalyst based on a bidentate phosphine ligand which is stabilized by at least one monodentate phosphine ligand.

EP-A-0 149 894 and U.S. Pat. No. 4,567,306 describe a continuous hydroformylation process using a hydroformylation catalyst which has a cyclic phosphite having a phosphorus atom as bridge head as ligand. Three oxygen atoms are bound directly to the phosphorus atom and at least two of these form a ring together with the phosphorus atom. Suitable ligands have, for example, a phosphabicyclo[2.2.2]octane or phosphaadamantyl skeleton. The process includes the stabilization of the ligands by means of a tertiary amine.

EP-A-0 155 508 and U.S. Pat. No. 4,599,206 describe hydroformylation processes using catalyst complexes based on diorganophosphite ligands, in which a liquid output can be taken from the reaction zone, brought into contact with a weak base anion exchanger and subsequently returned to the reaction zone. U.S. Pat. No. 4,717,775 describes a variant of the hydroformylation process disclosed in the abovementioned documents, according to which the hydroformylation is carried out in the presence of free diorganophosphite ligand. U.S. Pat. No. 4,774,361 describes a process for avoiding or minimizing the precipitation of rhodium from rhodium-phosphite catalyst complexes in a hydroformylation process having a liquid circuit, in which the aldehyde is distilled off from the reaction mixture and this distillation is carried out in the presence of an organic polymer containing at least three polar amide functions, for example polyvinylpyrrolidone or copolymers of vinylpyrrolidone and vinyl acetate. EP-A-0 276 231 has a disclosure content comparable to U.S. Pat. No. 4,774,361.

EP-A-214 622 describes a hydroformylation process using a catalyst based on a polyphosphite ligand which has from two to six phosphite groups. It is stated that the polyphosphite ligands can be stabilized if necessary by bringing the liquid output from the reaction zone into contact with a weak base anion-exchange resin before or after the product aldehydes have been separated off and only then recirculating the stream to the hydroformylation reactor.

WO 97/20794 and U.S. Pat. No. 5,741,942 describe methods of separating acidic phosphorus compounds from a reaction liquid comprising a metal-organophosphite catalyst complex and, if desired, free organophosphite ligands by treating the reaction liquid with an aqueous buffer solution which is able to remove at least part of the acidic phosphorus compounds. It is possible to use an additional organic nitrogen compound which is capable of reacting with the acidic phosphorus compounds, with the reaction product of nitrogen compound and phosphorus compound likewise being neutralized and removed by treatment with the aqueous buffer solution. Methods of stabilizing organophosphite ligands against hydrolytic degradation, of stabilizing metal-organophosphite catalyst complexes against deactivation and of reacting one or more reactants in the presence of metal-organophosphite catalyst complexes, in each of which a treatment with an aqueous buffer solution is carried out, have also been described. U.S. Pat. No. 5,741,944 describes an analogous method of separating acidic phosphorus compounds from hydroformylation product mixtures. U.S. Pat. No. 5,874,640 describes an analogous method of removing acidic phosphorus compounds from reaction product mixtures comprising metal catalyst complexes with organophosphorus ligands in general. Application of the method to reaction solutions containing phosphoramidite ligands is not described.

WO 97/20795, U.S. Pat. Nos. 5,741,943 and 5,741,945 describe processes which comprise reacting one or more reactants in the presence of a metal-organopolyphosphite catalyst complex and, if desired, free organopolyphosphite ligand and another, different sterically hindered organophosphorus ligand. The latter has the function of an indicator ligand which indicates depletion of the reaction mixture in polyorganophosphite ligands and at the same time is supposed to keep the rhodium in solution in the case of such a depletion.

WO 97/20797, U.S. Pat. Nos. 5,744,649 and 5,786,517 describe methods of removing acidic phosphorus compounds from reaction liquids comprising metal-organophosphite catalyst complexes by treatment with water. U.S. Pat. No. 5,886,235 describes an analogous method of treating reaction liquids which comprise metal complexes based on organophosphorus ligands as catalysts in quite general terms.

WO 97/20798 and U.S. Pat. No. 5,731,472 describe methods of stabilizing metal-organopolyphosphite catalyst complexes against deactivation, in which the catalyzed reaction is carried out in the presence of at least one free, heterocyclic nitrogen compound selected from among diazoles, triazoles, diazines and triazines.

WO 97/20799, U.S. Pat. Nos. 5,763,671 and 5,789,625 relate to methods of removing acidic phosphorus compounds from reaction liquids comprising metal-organophosphite catalyst complexes by extraction with water and treatment of the water with an acid-removing substance. U.S. Pat. No. 5,917,095 relates to an analogous method in which metal complexes based on organophosphorus ligands in general are used as catalysts.

WO 97/20800, U.S. Pat. Nos. 5,763,670 and 5,767,321 relate to processes in which organopolyphosphite catalyst complexes are used in the presence of a sufficient amount of free organopolyphosphite ligand to prevent or reduce hydrolytic degradation of the ligand and deactivation of the catalyst.

WO 97/20796, U.S. Pat. Nos. 5,763,677 and 5,763,680 describe methods of separating one or more acidic phosphorus compounds from reaction liquids comprising metal-organophosphite catalyst complexes by extraction with water and treatment of the water with an ion exchanger and optionally an amine. U.S. Pat. No. 5,892,119 describes an analogous method for reaction liquids which comprise metal complexes based on organophosphorus ligands in general as catalysts. Treatment of reaction liquids comprising catalysts based on phosphoramidite ligands is not described.

It is an object of the present invention to provide an improved process for the hydroformylation of compounds containing at least one ethylenically unsaturated double bond. It should use hydroformylation catalysts which make it possible for relatively long-chain, terminal or internal olefins or industrial mixtures of olefins having terminal and internal double bonds, e.g. mixtures of 1-butene and 2-butene, to be hydroformylated to give good yields of aldehydes having a higher linearity (n selectivity). A further requirement which the hydroformylation catalysts have to meet is good stability under hydroformylation conditions and thus a long catalyst operating life, since catalyst or ligand losses have a particularly adverse effect on the economics of a hydroformylation process.

It has now surprisingly been found that this object is achieved by a hydroformylation process in which a metal complex of a metal of transition group VIII of the Periodic Table of the Elements with at least one phosphoramidite compound as ligand dissolved in the reaction medium is used to catalyze the reaction and in which the solution is brought into contact with a base.

The invention accordingly provides a process for the hydroformylation of compounds containing at least one ethylenically unsaturated double bond by reaction with carbon monoxide and hydrogen in at least one reaction zone in the presence of a catalytically active fluid which comprises a dissolved metal complex of a metal of transition group VIII of the Periodic Table of the Elements with at least one phosphoramidite compound as ligand, wherein the fluid is brought into contact with a base.

BRIEF DESCRIPTIONS OF THE DRAWINGS

Figure 1:
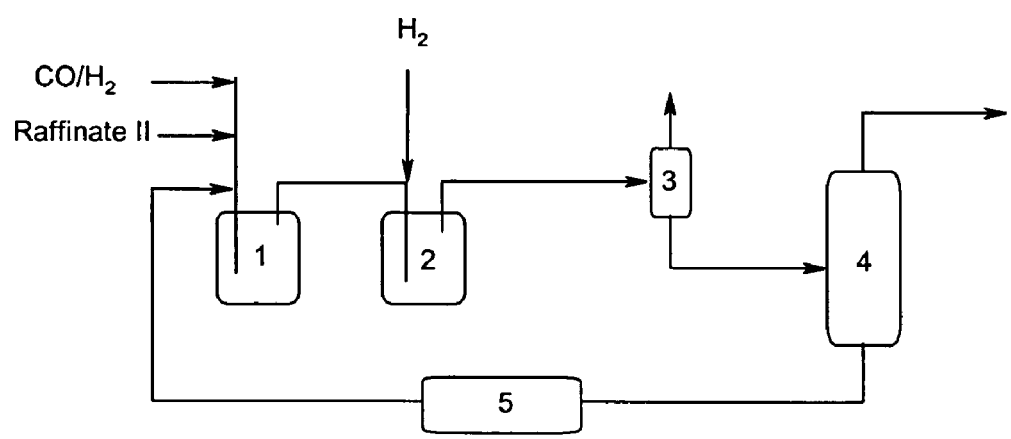
FIG. 1 shows a miniplant for carrying out continuous hydroformylations consisting of two autoclaves with lifting stirrer connected in series (1 and 2), a pressure separator (3), a flash stripping column (4), and an ion exchanger bed (5).

For the purposes of the present invention, a "phosphoramidite compound" is a phosphorus-containing compound having at least one phosphorus atom to which one, two or three groups are covalently bound via a nitrogen atom, i.e. to form a P—N bond. Phosphoramidite compounds, in particular those in which one or more substituted pyrrole groups are bound via their nitrogen atom to the phosphorus atom, and the hydroformylation catalysts based on them are known to have a good stability. The inventors of the present invention have now found that catalysts based on phosphoramidite ligands can be additionally stabilized against degradation of the ligands or deactivation of the catalysts under hydroformylation conditions by bringing the catalytically active fluid into contact with a base. This is surprising since these ligands already contain more or less basic nitrogen-containing groups. Advantageously, stabilization of the hydroformylation catalysts based on phosphoramidite ligands by bringing them into contact with a base is successful even in the absence of synthesis gas. The present invention therefore also provides a hydroformylation process comprising the work-up of the output from the reaction zone and recirculation of the catalytically active fluid, with at least one of these steps being carried out in the absence of carbon monoxide and hydrogen.

For the purposes of the present invention, "bringing into contact" refers both to formation of a single-phase mixture and to contacting via a phase interface, e.g. liquid/liquid or liquid/solid. The contacting can be carried out over the total duration of the hydroformylation (including the work-up and recirculation of the catalytically active fluid), part thereof or periodically.

The catalytically active fluid comprises at least one dissolved metal complex of a metal of transition group VIII of the Periodic Table of the Elements with at least one phosphoramidite compound as ligand. The metal complex is thus generally present as a homogeneous single-phase solution in a suitable solvent. This solution can further comprise phosphoramidite compounds as free ligands. As solvents, preference is given to using the relatively high-boiling subsequent reaction products formed in the hydroformylation of the respective ethylenically unsaturated compounds, e.g. the products of aldol condensation. Furthermore, the hydroformylation products can also function as solvents until they are separated off.

Aromatics such as toluene and xylenes, hydrocarbons or mixtures of hydrocarbons are likewise suitable as solvents. Further suitable solvents are esters of aliphatic carboxylic acids with alkanols, for example ethyl acetate or Texanol®, ethers such as tert-butyl methyl ether and tetrahydrofuran. In the case of sufficiently hydrophilic ligands, it is also possible to use alcohols such as methanol, ethanol, n-propanol, isopropanol, n-butanol, isobutanol, ketones such as acetone and methyl ethyl ketone, etc. Furthermore, "ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)phosphonium salts, e.g. the tetrafluoroborates, acetates, tetrachloroaluminates, hexafluorophosphates, chlorides and tosylates.

The hydroformylation is carried out in at least one reaction zone which can comprise one or more, identical or different reactors. In the simplest case, the reaction zone is formed by a single reactor. Both the reactors of each individual zone and the reactors which may form different stages can in each case have identical or different mixing characteristics. The reactors can, if desired, be divided one or more times by means of internals. If two or more reactors form one zone, these can be connected in any desired way, e.g. in parallel or in series.

Suitable pressure-rated reaction apparatuses for the hydroformylation are known to those skilled in the art. They include the generally customary reactors for gas-liquid reactions, e.g. tube reactors, stirred vessels, gas circulation reactors, bubble columns, etc., which may, if appropriate, be divided by internals.

Carbon monoxide and hydrogen are usually used in the form of a mixture known as synthesis gas. The composition of the synthesis gas used in the process of the invention can vary within a wide range. The molar ratio of carbon monoxide to hydrogen is generally from 1:1000 to 1000:1, preferably from 1:100 to 100:1. If a plurality of reaction zones are used, these can have identical or different molar ratios of CO to $H_2$.

The temperature in the hydroformylation reaction is generally in the range from about 20 to 200° C., preferably from about 50 to 190° C., in particular from about 60 to 150° C. The reaction is preferably carried out at a pressure in the range from about 1 to 700 bar, particularly preferably from 3 to 600 bar, in particular from 5 to 50 bar. The reaction pressure can be varied as a function of the activity of the hydroformylation catalyst used. Thus, the hydroformylation catalysts described in more detail below sometimes allow a reaction in a lower pressure range, for instance in the range from about 1 to 100 bar. If a plurality of reaction zones are used, these can be operated at identical or different temperatures and/or pressures.

The hydroformylation can be carried out batchwise or continuously. Preference is given to a continuous process wherein a) the ethylenically unsaturated compound(s) and carbon monoxide and hydrogen are fed into the reaction zone(s) and are reacted in the presence of the catalytically active fluid, b) an output is taken from the reaction zone and is subjected to a fractionation to give a fraction consisting essentially of the hydroformylation product and a fraction comprising the catalytically active fluid in which the by-products of the hydroformylation which have boiling points higher than that of the hydroformylation product are present and the metal complex is dissolved, and c) the catalytically active fluid is, if appropriate after separating off at least part of the by-products having boiling points higher than that of the hydroformylation product, recirculated to the reaction zone.

The output from the reaction zone is subjected to a single-stage or multistage separation operation to give a stream comprising the major part of the hydroformylation product and a stream comprising the catalytically active fluid. Depending on the discharge and separation methods employed, further streams are generally obtained, e.g. off-gases comprising synthesis gas, streams comprising unreacted ethylenically unsaturated compound with or without saturated hydrocarbon etc. These can be recirculated partly or in their entirety to the reaction zone or be discharged from the process.

Preference is given to taking a liquid output from the reaction zone (liquid discharge process). This liquid output comprises, as significant constituents:

i) the hydroformylation product, i.e. the aldehydes produced from the olefin or olefin mixture used, ii) the high-boiling by-products of the hydroformylation, as result from, for example, the aldol reaction of the aldehydes formed, iii) the homogeneously dissolved hydroformylation catalyst and possibly free ligand, iv) possibly unreacted olefins, v) low-boiling components such as alkanes, and vi) dissolved synthesis gas.

If an inert solvent is used for the hydroformylation, this is also present in the liquid output from the reaction zone. However, the by-products which are formed in the hydroformylation (e.g. by aldol condensation) and have boiling points higher than that of the hydroformylation product are generally used as solvent.

The fractionation of the liquid output from the reaction zone to give firstly a fraction consisting essentially of the hydroformylation product and, secondly, the catalytically active fluid in which the by-products of the hydroformylation which have boiling points higher than that of the hydroformylation product are present and the metal complex is dissolved is carried out by conventional methods known to those skilled in the art. These include depressurization and thermal fractionation steps (distillations). Suitable separation apparatuses for a distillation are, for example, distillation columns such as tray columns which may, if desired, be equipped with bubble caps, sieve plates, sieve trays, valves, etc., evaporators such as thin film evaporators, falling film evaporators, wiped film evaporators, etc.

The liquid output from the reaction zone can, for example, be worked up by firstly subjecting it to a single-stage or multistage degassing operation.

In one embodiment with single-stage degassing, the liquid output from the reaction zone is, for example, depressurized into a depressurization vessel and, as a result of the reduction in pressure, the output is separated into a liquid phase comprising the hydroformylation catalyst and, if present, free ligands, the high-boiling by-products of the hydroformylation and a gaseous phase comprising the major part of the hydroformylation product formed, any unreacted olefins, low-boiling components and excess synthesis gas. The liquid phase forming the catalytically active fluid can, in order to recycle the catalyst, be returned as a recycle stream, if appropriate after separating off at least part of the high-boiling by-products, to the reaction zone. The gas phase can be worked up further by passing it to, for example, a condenser in which the hydroformylation product is separated off in liquid form. The gas phase obtained in the condenser, which consists essentially of unreacted synthesis gas, unreacted olefin and inert components, can, if appropriate after separating off at least part of the inert components, be returned either wholly or partly to the reaction zone.

In a further embodiment of the liquid discharge process with degassing, the liquid output from the reaction zone is worked up by subjecting to a two-stage degassing operation. Here, the first degassing stage can also be configured as a calming zone in which no gas is introduced into the liquid phase. The gas phase obtained in this calming/depressurization stage consists essentially of synthesis gas. The liquid phase obtained from the calming/depressurization stage can in turn be separated into a liquid phase and a gas phase in a second depressurization stage (degassing stage). The second liquid phase obtained in this way generally comprises the by-products having boiling points higher than that of the hydroformylation product, the homogeneously dissolved first hydroformylation catalyst and possibly part of the hydroformylation product. The second gas phase comprises the unreacted olefin, saturated hydrocarbons and likewise part of the hydroformylation product. To isolate firstly the catalytically active fluid and secondly a fraction comprising the major part of the hydroformylation product, the second depressurization stage can be followed by a thermal work-up. This thermal separation step can be, for example, a distillation. In the distillation, the second liquid phase and the second gas phase from the second depressurization step are preferably conveyed in countercurrent and thus brought into particularly intimate contact (stripping). In a preferred embodiment, the second depressurization stage is configured as a combination of the depressurization step (flash) with a thermal separation step (flash/stripping stage).

As an alternative to the above-described pure liquid discharge processes, it is also possible to use the gas recycle process in which a further gaseous output is taken from the gas space of the reaction zone. This gaseous output consists essentially of synthesis gas, unreacted olefins and inert components, and, depending on the vapor pressure of the hydroformylation product in the reaction zone, part of the hydroformylation products formed may also be discharged in this gaseous output. The hydroformylation product carried out with the gas stream can be condensed out by, for example, cooling and the gas stream which has been freed of the liquid fraction can be returned to the reaction zone.

The bases used in the process of the invention are preferably selected from among bases soluble in the catalytically active fluid, bases immobilized on a solid phase and combinations thereof. The base is preferably selected from among basic nitrogen compounds.

Particularly preferred bases are nitrogen compounds which have no primary and secondary nitrogen atoms (i.e. ones to which H atoms are still bound). Basic nitrogen compounds which contain compounds having primary and secondary nitrogen atoms as impurities, e.g. tertiary amines which are, as a result of the method by which they are produced, contaminated with primary and/or secondary amines, can be subjected to a work-up to remove at least part of these compounds before they are used in the process of the invention.

Suitable bases are, for example, trialkylamines. Trialkylamines which have a boiling point below or in the region of that of the product aldehydes, as is generally the case for tri($C_1$-$C_3$-)alkylamines, are less suitable if the product aldehydes are separated from the reaction product mixture by distillation.

Preference is also given to the base being selected from among dialkylarylamines, preferably di($C_1$-$C_4$-)alkylarylamines, where the alkyl groups and/or the aryl group may be substituted further. The aryl group is preferably phenyl. Such compounds include, for example, N,N-dimethylaniline, N,N-diethylaniline, N,N,2,4,6-pentamethylaniline, bis(4-(N,N-dimethylamino)phenyl)methylene, 4,4'-bis(N,N-dimethylamino)benzo-phenone, etc.

Preference is also given to the base being selected from among alkyldiarylamines, preferably ($C_1$-$C_4$-)alkyldiarylamines, where the alkyl group and/or the aryl group may be substituted. Such compounds include, for example, diphenylmethylamine and diphenylethylamine.

Preference is also given to the base being selected from among triarylamines, where the aryl groups may be substituted, for example triphenylamine, etc. Further preferred amines are tricycloalkylamines, such as tricyclohexylamine.

Preference is also given to the base being selected from among nitrogen-containing heterocycles. The nitrogen-containing heterocycles are preferably selected from the group consisting of pyrroles, pyrrolidines, pyridines, quinolines, isoquinolines, purines, pyrazoles, imidazoles, triazoles, tetrazoles, indolizines, pyridazines, pyrimidines, pyrazines, triazines, indoles, isoindoles, oxazoles, oxazolidones, oxazolidines, morpholines, piperazines, piperidines and derivatives thereof.

Suitable derivatives of the abovementioned nitrogen-containing heterocycles can have, for example, one or more $C_1$-$C_6$-alkyl substituents such as methyl, ethyl, n-propyl, isopropyl, n-butyl, sec-butyl, tert-butyl, etc.

Heterocycles preferred as bases are pyrroles, indoles, pyridines, quinolines and triazoles, which may additionally bear one or more $C_1$-$C_6$-alkyl substituents. Such compounds include, for example, 3-alkylindoles, such as 3-methylindole, 2,6-dialkylpyridines, such as 2,6-dimethylpyridine, quinoline and 1-H-benzotriazole.

The abovementioned bases can be used either individually or in the form of any mixtures.

When at least one base which is soluble in the catalytically active fluid is used, a molar ratio of base to phosphoramidite compound of from 0.01:1 to 5:1, preferably from 0.1:1 to 1.5:1, is preferably maintained in the reaction zone. For this purpose, for example, the pH of the reaction mixture can be monitored at regular intervals and base can be added to the reaction mixture if necessary.

If the work-up of the reaction output encompasses, as described above, a thermal separation step, preference is given to using high-boiling soluble bases which have a boiling point under the conditions of the thermal work-up which is sufficiently above those of the hydroformylation products.

The output from the reaction zone is preferably fractionated so that the resulting fraction comprising the hydroformylation product is essentially free of the base used. The fractionation of the output from the reaction zone is preferably also carried out so that essentially all the base is present in the fraction forming the catalytically active fluid and is recirculated to the reaction zone together with this.

In one embodiment of the process of the invention, at least one base immobilized on a solid phase is used as base. Suitable immobilized bases are in principle the basic ion exchangers known to those skilled in the art. The solid phase of these basic ion exchangers comprises, for example, a polymer matrix. Such matrices include, for example, polystyrene matrices which comprise copolymers of styrene and at least one crosslinking monomer, e.g. divinylbenzene, together with, if appropriate, further comonomers. Further suitable matrices are polyacrylic matrices obtained by polymerization of at least one (meth)acrylate, at least one crosslinking monomer and, if appropriate, further comonomers. Suitable polymer matrices also include phenol-formaldehyde resins and polyalkylamine resins which are obtained, for example, by condensation of polyamines with epichlorohydrin.

The anchor groups which are bound to the solid phase either directly or via a spacer group (and whose loosely bound counterions can be replaced by ions bearing a charge of the same sign) are preferably selected from among nitrogen-containing groups, preferably tertiary and quaternary amino groups. Preference is given to anchor groups which are present in the free base form.

Examples of suitable functional groups are (in order of decreasing basicity):
—$CH_2N^+(CH_3)_3OH^-$ e.g. Duolite A 101
—$CH_2N^+(CH_3)_2CH_2CH_2OH$ $OH^-$ e.g. Duolite A 102
—$CH_2N(CH_3)_2$ e.g. Amberlite IRA 67
—$CH_2NHCH_3$
—$CH_2NH_2$ e.g. Duolite A 365

Both strongly basic and weakly basic ion exchangers are suitable for the process of the invention, with preference being given to weakly basic ion exchangers. Among weakly basic ion exchangers, preference is given to those containing tertiary amino groups. Strongly basic ion exchangers generally have quaternary ammonium groups as anchor groups. A weakly basic ion exchanger is generally present in the free base form after regeneration.

Commercially available ion exchangers suitable for the process of the invention are, for example, Amberlite® IRA 67 and Amberlyst A21.

Ion exchangers usually have a hydrophilic sphere of bound water. The bases immobilized on a solid phase are preferably brought into contact with at least one anhydrous solvent to remove part or all of the bound water before they are used in the process of the invention. In such a case, preference is given to firstly treating the ion exchanger with a water-soluble or water-miscible solvent and subsequently with an essentially water-insoluble solvent. Suitable water-miscible solvents are, for example, alcohols such as methanol, ethanol, n-propanol, isopropanol etc. Suitable essentially water-insoluble solvents are, for example, aromatics such as toluene and xylenes, hydrocarbons and hydrocarbon mixtures and also high-boiling alcohols, e.g. 2-propylheptanol. It has surprisingly been found that the ion exchangers used according to the invention are also suitable for stabilizing phosphoramidite compounds against degradation or protecting the corresponding hydroformylation catalysts from deactivation in an essentially water-free medium.

The catalytically active fluid is preferably brought into contact with an immobilized base by taking a liquid output from the reaction zone and bringing it into contact with the immobilized base before or after it is fractionated. Preference is given to the fraction forming the catalytically active fluid which is obtained by fractionation of the output being brought into contact with the immobilized base. The base can be present either in the form of a slurry or in the form of packing, e.g. as a fixed bed.

The regeneration of the immobilized base is carried out by conventional methods known to those skilled in the art, e.g. treatment with aqueous base. Suitable bases are, for example, ammonium, alkali metal carbonates such as sodium carbonate and potassium carbonate, and alkali metal hydroxides such as sodium hydroxide and potassium hydroxide. Preference is given to firstly carrying out the treatment with one of the abovementioned water-soluble or water-miscible solvents before regeneration. Regeneration is preferably followed by at least one rinsing step using a dry organic solvent, as described above. Here too, particular preference is given to firstly carrying out a treatment with a water-soluble or water-miscible solvent and subsequently with an essentially water-insoluble solvent.

In a preferred embodiment of the process of the invention, a combination of at least one base soluble in the catalytic fluid and at least one base immobilized on a solid phase is used. The base pairs are selected so that the immobilized bases are capable of at least partly liberating the soluble bases from the acid-base adducts obtained by reaction of the soluble bases with acids. For this purpose, the bases are selected so that the base strengths of the liquid bases under the reaction conditions are lower than the base strengths of the immobilized bases. These base strengths can readily be determined by a person skilled in the art by means of simple routine experiments. A good guide is provided by the $pK_b$ values for the bases which are generally known for use in aqueous systems.

Phosphoramidite compounds suitable for use in the process of the invention are described in WO 00/56451, WO 02/083695, WO 03/018192 and the German patent application 102 43 138.8, which are hereby fully incorporated by reference.

The metal of transition group VIII of the Periodic Table is preferably Co, Ru, Rh, Pd, Pt, Os or Ir, especially Rh, Co, Ir or Ru.

In the following, the expression "alkyl" encompasses straight-chain and branched alkyl groups. The alkyl groups are preferably straight-chain or branched $C_1$-$C_{20}$-alkyl groups, more preferably $C_1$-$C_{12}$-alkyl groups, particularly preferably $C_1$-$C_8$-alkyl groups and very particularly preferably $C_1$-$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also encompasses substituted alkyl groups which can generally bear 1, 2, 3, 4 or 5 substituents, preferably 1, 2 or 3 substituents and particularly preferably 1 substituent, selected from among the groups cycloalkyl, aryl, hetaryl, halogen, $NE^1E^2$, $NE^1E^2E^{3+}$, COOH, carboxylate, —SO₃H and sulfonate, where $E^1$, $E^2$ and $E^3$ are identical or different radicals selected from among hydrogen, alkyl, cycloalkyl and aryl.

For the purposes of the present invention, the expression "alkylene" refers to straight-chain or branched alkanediyl groups having from 1 to 4 carbon atoms.

For the purposes of the present invention, the expression "cycloalkyl" encompasses both unsubstituted and substituted cycloalkyl groups, preferably $C_5$-$C_7$-cycloalkyl groups, such as cyclopentyl, cyclohexyl or cycloheptyl, which, if they are substituted, can generally bear 1, 2, 3, 4 or 5 substituents, preferably 1, 2 or 3 substituents and particularly preferably 1 substituent, selected from among the groups alkyl, alkoxy and halogen.

For the purposes of the present invention, the expression "heterocycloalkyl" encompasses saturated, cycloaliphatic groups which generally have from 4 to 7, preferably 5 or 6, ring atoms and in which 1 or 2 of the ring carbons are replaced by heteroatoms selected from among the elements oxygen, nitrogen and sulfur and which may be substituted. If they are substituted, these heterocycloaliphatic groups can bear 1, 2 or 3 substituents, preferably 1 or 2 substituents, particularly preferably 1 substituent, selected from among alkyl, aryl, COOR$^f$ (R$^f$=hydrogen, alkyl, cycloalkyl or aryl), COO⁻M⁺ and NE$^1$E$^2$, preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

For the purposes of the present invention, the expression "aryl" encompasses both unsubstituted and substituted aryl groups and preferably refers to phenyl, tolyl, xylyl, mesityl, naphthyl, fluorenyl, anthracenyl, phenanthrenyl or naphthacenyl, particularly preferably phenyl or naphthyl. If they are substituted, these aryl groups can generally bear 1, 2, 3, 4 or 5 substituents, preferably 1, 2 or 3 substituents and particularly preferably 1 substituent, selected from among the groups alkyl, alkoxy, carboxyl, carboxylate, trifluoromethyl, —SO₃H, sulfonate, NE$^1$E$^2$, alkylene-NE$^1$E$^2$, nitro, cyano and halogen.

For the purposes of the present invention, the expression "hetaryl" refers to unsubstituted or substituted, heterocycloaromatic groups, preferably the groups pyridyl, quinolinyl, acridinyl, pyridazinyl, pyrimidinyl, pyrazinyl, and also the subgroup of "pyrrole groups". If they are substituted, these heterocycloaromatic groups can generally bear 1, 2 or 3 substituents selected from among the groups alkyl, alkoxy, carboxyl, carboxylate, —SO₃H, sulfonate, NE$^1$E$^2$, alkylene-NE$^1$E$^2$, trifluoromethyl or halogen.

For the purposes of the present invention, the expression "pyrrole group" refers to a series of unsubstituted or substituted, heterocycloaromatic groups which are derived structurally from the pyrrole skeleton and have a pyrrolic nitrogen atom in the heterocycle which can be linked covalently to other atoms, for example a pnicogen atom. The expression "pyrrole group" thus encompasses the unsubstituted or substituted groups pyrrolyl, imidazolyl, pyrazolyl, indolyl, purinyl, indazolyl, benzotriazolyl, 1,2,3-triazolyl, 1,3,4-triazolyl and carbazolyl, which, if they are substituted, can generally bear 1, 2 or 3 substituents, preferably 1 or 2 substituents, particularly preferably 1 substituent, selected from among the groups alkyl, alkoxy, acyl, carboxyl, carboxylate, —SO₃H, sulfonate, NE$^1$E$^2$, alkylene-NE$^1$E$^2$, trifluoromethyl and halogen. A preferred substituted indolyl group is the 3-methylindolyl group.

Accordingly, the expression "bispyrrole group" encompasses, for the purposes of the present invention, divalent groups of the formula Py-I-Py, which contain two pyrrole groups bound via a direct chemical bond or a link comprising alkylene, oxa, thio, imino, silyl or alkylimino groups, for example the bisindole diyl group of the formula

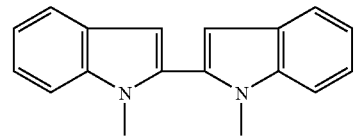

as an example of a bispyrrole group containing two directly linked pyrrole groups, in this case indolyl, or the bispyrrole diylmethane group of the formula

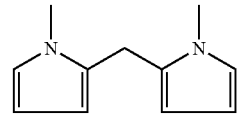

as an example of a bispyrrole group containing two pyrrole groups, in this case pyrrolyl, linked via a methylene group. Like the pyrrole groups, the bispyrrole groups can also be unsubstituted or substituted and, if they are substituted, generally bear 1, 2 or 3 substitutents, preferably 1 or 2 substituents, in particular 1 substituent, selected from among alkyl, alkoxy, carboxyl, carboxylate, —SO₃H, sulfonate, NE$^1$E$^2$, alkylene-NE$^1$E$^2$, trifluoromethyl and halogen per pyrrole group unit. In these indications of the number of possible substituents, the link between the pyrrole group units via a direct chemical bond or via the link comprising the above-mentioned groups is not regarded as substitution.

For the purposes of the present invention, carboxylate and sulfonate are preferably derivatives of a carboxylic acid function or a sulfonic acid function, in particular a metal carboxylate or sulfonate, a carboxylic ester or sulfonic ester function or a carboxamide or sulfonamide function. Such functions include, for example, the esters with $C_1$-$C_4$-alkanols, such as methanol, ethanol, n-propanol, isopropanol, n-butanol, sec-butanol and tert-butanol, and also primary amides and their N-alkyl and N,N-dialkyl derivatives.

What has been said above with regard to the expressions "alkyl", "cycloalkyl", "aryl", "heterocycloalkyl" and "hetaryl" applies analogously to the expressions "alkoxy", "cycloalkoxy", "aryloxy", "heterocycloalkoxy" and "hetaryloxy".

For the purposes of the present invention, the expression "acyl" refers to alkanoyl or aroyl groups which generally have from 2 to 11, preferably from 2 to 8 carbon atoms, for example the acetyl, propanoyl, butanoyl, pentanoyl, hexanoyl, heptanoyl, 2-ethylhexanoyl, 2-propylheptanoyl, benzoyl or naphthoyl group.

The radicals $E^1$ to $E^{12}$ are selected independently from among hydrogen, alkyl, cycloalkyl and aryl. The groups NE$^1$E$^2$, NE$^4$E$^5$, NE$^7$E$^8$ and NE$^{10}$E$^{11}$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine or iodine, preferably fluorine, chlorine or bromine.

$M^+$ is a cation equivalent, i.e. a monovalent cation or the part of a polyvalent cation corresponding to a single positive charge. The cation $M^+$ serves merely as counterion to neutralize negatively charged substituent groups such as the $COO^-$ or sulfonate group and can in principle be selected freely. Preference is therefore given to using alkali metal ions, in particular $Na^+$, $K^+$, $Li^+$ ions, or onium ions such as ammonium, monoalkylammonium, dialkylammonium, trialkylammonium, tetraalkylammonium, phosphonium, tetraalkylphosphonium or tetraarylphosphonium ions.

An analogous situation applies to the anion equivalent $X^-$, which serves merely as counterion of positively charged substituent groups such as ammonium groups and can be selected freely from among monovalent anions and the parts of a polyvalent anion corresponding to a single negative charge. Suitable anions are, for example, halide ions $X^-$, such as chloride and bromide. Preferred anions are sulfate and sulfonate, e.g. $SO_4^{2-}$, tosylate, trifluoromethanesulfonate and methylsulfonate.

x and y are each an integer from 1 to 240, preferably an integer from 3 to 120.

Fused ring systems can be aromatic, hydroaromatic and cyclic compounds joined by fusion. Fused ring systems comprise two, three or more rings. Depending on the way the rings are linked, a distinction is made in the case of fused ring systems between ortho-fusion, i.e. each ring shares an edge or two atoms with each adjacent ring, and peri-fusion in which one carbon atom belongs to more than two rings. Among fused ring systems, preference is given to ortho-fused ring systems.

The phosphoramidite compound used in the process of the invention is preferably selected from among compounds of the formulae I and II

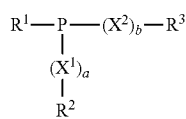
(I)

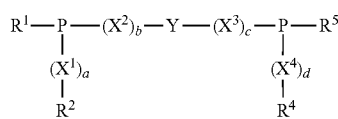
(II)

where $R^1$ and $R^5$ are each, independently of one another, pyrrole groups bound via the nitrogen atom to the phosphorus atom, $R^2$, $R^3$ and $R^4$ are each, independently of one another, alkyl, cycloalkyl, heterocycloalkyl, aryl or hetaryl, or $R^1$ together with $R^2$ and/or $R^4$ together with $R^5$ forms a divalent group containing at least one pyrrole group bound via the pyrrolic nitrogen atom to the phosphorus atom, Y is a divalent bridging group having from 2 to 20 bridge atoms between the flanking bonds, $X^1$, $X^2$, $X^3$ and $X^4$ are selected independently from among O, S, $SiR^\alpha R^\beta$ and $NR^\gamma$, where $R^\alpha$, $R^\beta$ and $R^\gamma$ are each, independently of one another, hydrogen, alkyl, cycloalkyl, heterocycloalkyl, aryl or hetaryl, and a, b, c and d are each, independently of one another, 0 or 1.

The radicals $R^2$, $R^3$ and $R^4$ in the formulae (I) and (II) can be, independently of one another, alkyl, cycloalkyl, heterocycloalkyl, aryl or hetaryl, where the alkyl radicals may have 1, 2, 3, 4 or 5 substituents selected from among cycloalkyl, heterocycloalkyl, aryl, hetaryl, alkoxy, cycloalkoxy, heterocycloalkoxy, aryloxy, hetaryloxy, hydroxy, thiol, polyalkylene oxide, polyalkylenimine, COOH, carboxylate, $SO_3H$, sulfonate, $NE^7E^8$, $NE^7E^8E^{9+}X^-$, halogen, nitro, acyl and cyano, where $E^7$, $E^8$ and $E^9$ are identical or different radicals selected from among hydrogen, alkyl, cycloalkyl and aryl and $X^-$ is an anion equivalent, and the cycloalkyl, heterocycloalkyl, aryl and hetaryl radicals $R^2$, $R^3$ and $R^4$ may each have 1, 2, 3, 4 or 5 substituents selected from among alkyl and the substituents mentioned above for the alkyl radicals $R^2$, $R^3$ and $R^4$.

The substituents $R^2$, $R^3$ and/or $R^4$ are advantageously also pyrrole groups bound via the pyrrolic nitrogen atom to the phosphorus atom.

The phosphoramidite compounds used in the process of the invention are particularly preferably selected from among chelating phosphoramidites. Particularly preferred chelating phosphoramidites are the phosphoramidite compounds of the formula II.1

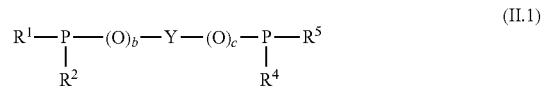
(II.1)

where $R^1$, $R^2$, $R^4$, $R^5$, Y, b and c are as defined above.

In a first preferred embodiment, the substituents $R^1$, $R^2$, $R^4$ and $R^5$ are pyrrole groups bound via the pyrrolic nitrogen atom to the phosphorus atom, with $R^1$ not being bound to $R^2$ and $R^4$ not being bound to $R^5$. The meaning of the term pyrrole group here corresponds to the definition given above.

Preference is given to chelating phosphorus compounds in which the radicals $R^1$, $R^2$, $R^4$ and $R^5$ are selected independently from among groups of the formulae III.a to III.k

(III.a)

(III.b)

(III.c)

(III.d)

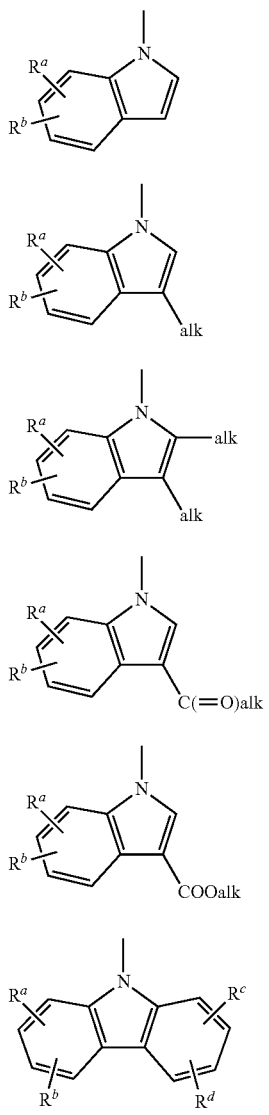
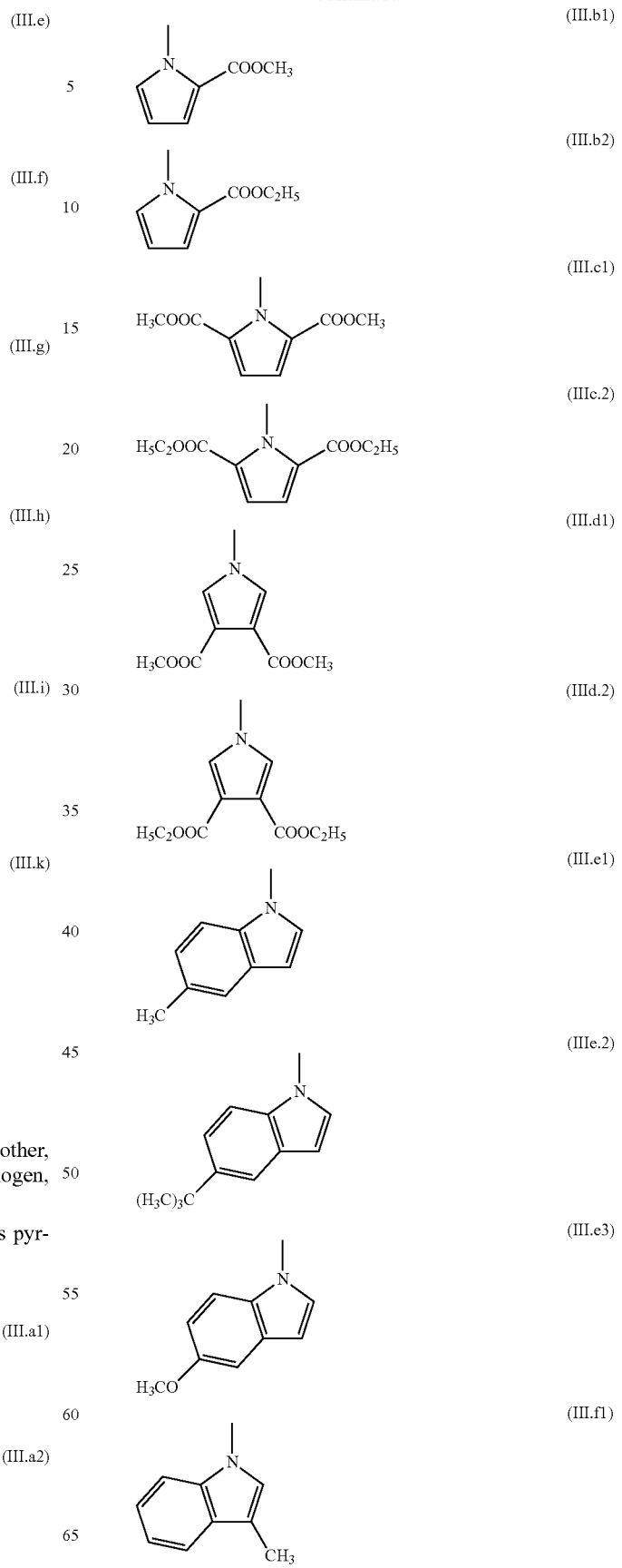
where
alk is a $C_1$-$C_{12}$-alkyl group and
$R^a$, $R^b$, $R^c$ and $R^d$ are each, independently of one another, hydrogen, $C_1$-$C_4$-alkyl, $C_1$-$C_4$-alkoxy, acyl, halogen, $C_1$-$C_4$-alkoxycarbonyl or carboxyl.
For the purposes of illustration, some advantageous pyrrole groups are listed below:
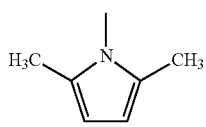
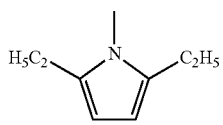

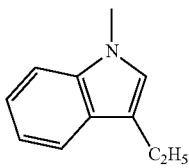
(III.f2)

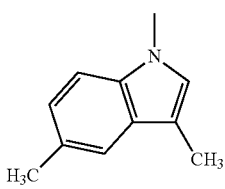
(III.f3)

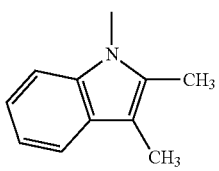
(III.g1)

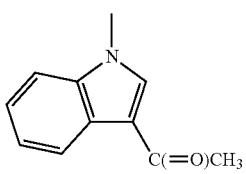
(III.h1)

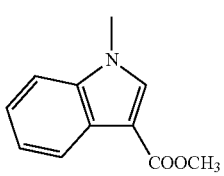
(III.i1)

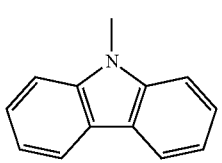
(III.k1)

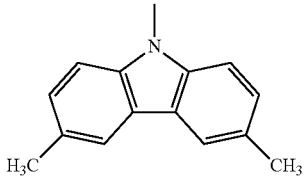
(III.k2)

A particularly advantageous group is the 3-methylindolyl group (skatolyl group) of the formula III.f1. Hydroformylation catalysts based on ligands having one or more 3-methylindolyl group(s) bound to the phosphorus atom have a particularly high stability and thus particularly long catalyst operating lives even without stabilization by a base.

In a further advantageous embodiment of the present invention, the substituent $R^1$ together with the substituent $R^2$ and/or the substituent $R^4$ together with the substituent $R^5$ in the formulae I, II and II.1 can form a divalent group comprising a pyrrole group bound via the pyrrolic nitrogen atom to the phosphorus atom and having the formula Py-I—W, where
Py is a pyrrole group,
I is a chemical bond or O, S, $SiR^\pi R^\chi$, $NR^\omega$ or optionally substituted $C_1$-$C_{10}$-alkylene, preferably $CR^\lambda R^\mu$,
W is cycloalkyloxy or cycloalkylamino, aryloxy or arylamino, hetaryloxy or hetarylamino
and
$R^\pi$, $R^\chi$, $R^\omega$, $R^\lambda$ and $R^\mu$ are each, independently of one another, hydrogen, alkyl, cycloalkyl, heterocycloalkyl, aryl or hetaryl,
where the terms used here have the meanings indicated above. Preferred divalent groups of the formula Py-I—W are, for example:

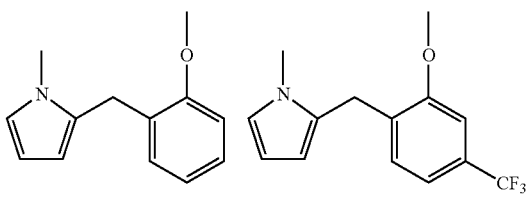

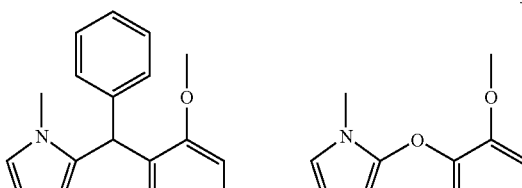

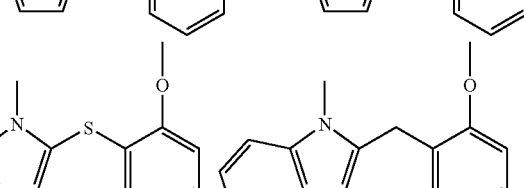

Preference is given to phosphoramidites in which the substituent $R^1$ together with the substituent $R^2$ and/or the substituent $R^4$ together with the substituent $R^5$ forms a bispyrrole group of the formula

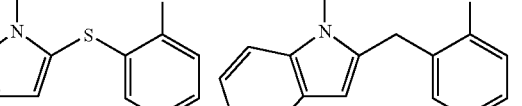

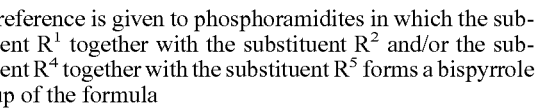

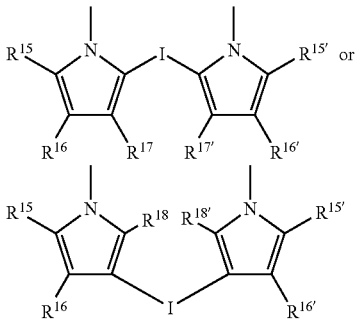

where
I is a chemical bond or O, S, $SiR^\pi R^\chi$, $NR^\omega$ or optionally substituted $C_1$-$C_{10}$-alkylene, preferably $CR^\lambda R^\mu$, where $R^\pi$, $R^\chi$, $R^\omega$, $R^\lambda$ and $R^\mu$ are each, independently of one another, hydrogen, alkyl, cycloalkyl, heterocycloalkyl, aryl or hetaryl,
$R^{15}$, $R^{15'}$, $R^{16}$, $R^{16'}$, $R^{17}$, $R^{17'}$, $R^{18}$ and $R^{18'}$ are each, independently of one another, hydrogen, alkyl, cycloalkyl, heterocycloalkyl, aryl, hetaryl, W'COOR$^f$, W'COO$^-$M$^+$, W'(SO$_3$)R$^f$, W'(SO$_3$)$^-$M$^+$, W'PO$_3$(R$^f$)(R$^g$), W'(PO$_3$)$^{2-}$(M$^+$)$_2$, W'NE$^{10}$E$^{11}$, W'(NE$^{10}$E$^{11}$E$^{12}$)$^+$X$^-$, W'OR$^f$, W'SR$^f$, (CHR$^g$CH$_2$O)$_x$R$^f$, (CH$_2$NE$^{10}$)$_x$R$^f$, (CH$_2$CH$_2$NE$^{10}$)$_x$R$^f$, halogen, trifluoromethyl, nitro, acyl or cyano, where W' is a single bond, a heteroatom, a heteroatom-containing group or a divalent bridging group having from 1 to 20 bridge atoms, R$^f$, E$^{10}$, E$^{11}$, E$^{12}$ are identical or different radicals selected from among hydrogen, alkyl, cycloalkyl and aryl, R$^g$ is hydrogen, methyl or ethyl, M$^+$ is a cation equivalent, X$^-$ is an anion equivalent and x is an integer from 1 to 240, where two adjacent radicals R$^{15}$ and R$^{16}$ and/or R$^{15'}$ and R$^{16'}$ together with the carbon atoms of the pyrrole ring to which they are bound may also form a fused ring system having 1, 2 or 3 further rings.

I is preferably a chemical bond or a C$_1$-C$_4$-alkylene group, particularly preferably a methylene group.

For the purposes of illustration, a few advantageous "bispyrrolyl groups" are listed below:

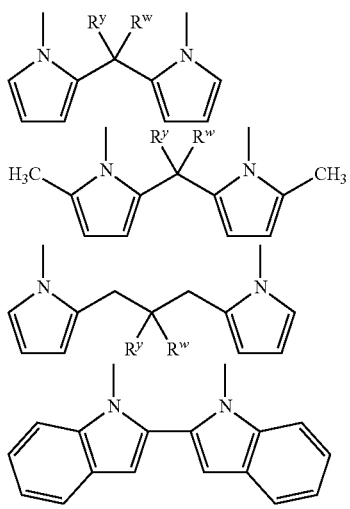

a: R$^y$, R$^w$ = H
b: R$^y$ = H
   R$^w$ = C$_6$H$_5$
c: (R$^y$ + R$^w$) = C$_4$H$_8$

In a preferred embodiment, the bridging group Y in the formulae (I), (II) and (II.1) is selected from among groups of the formulae IV.a to IV.u

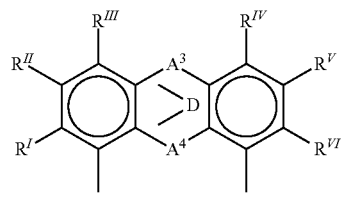
(IV.a)

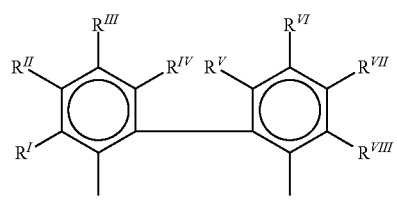
(IV.b)

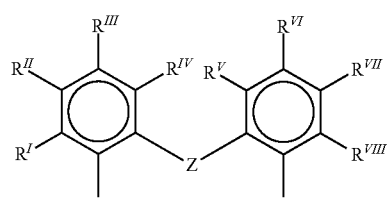
(IV.c)

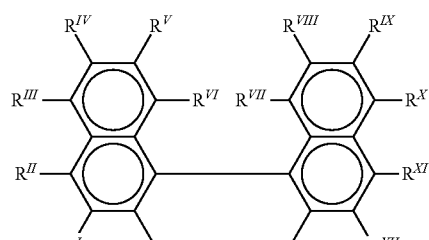
(IV.d)

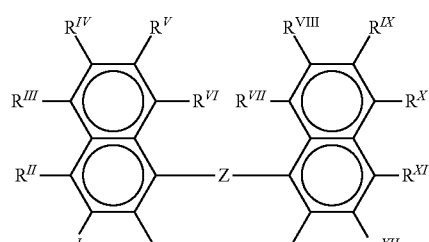
(IV.e)

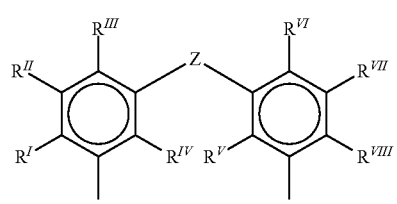
(IV.f)

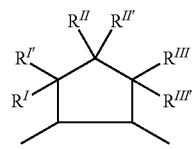
(IV.g)

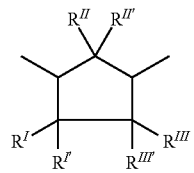
(IV.h)

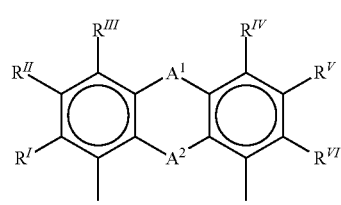
(IV.i)

-continued

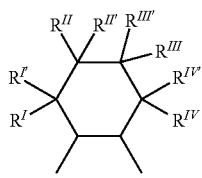
(IV.k)

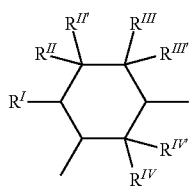
(IV.l)

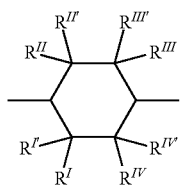
(IV.m)

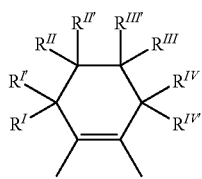
(IV.n)

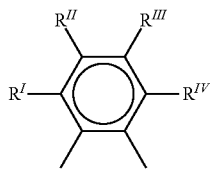
(IV.o)

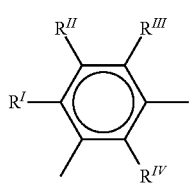
(IV.p)

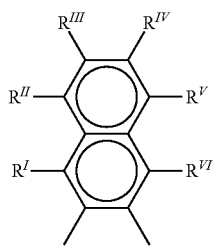
(IV.q)

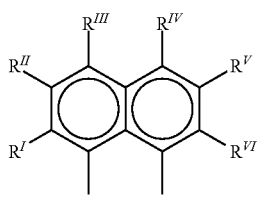
(IV.r)

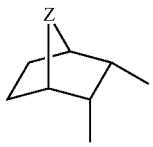
(IV.s)

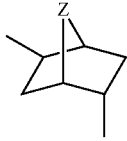
(IV.t)

(IV.u)

where
$R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$ and $R^{XII}$ are each, independently of one another, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, where $E^1$ and $E^2$ are identical or different radicals selected from among hydrogen, alkyl, cycloalkyl and aryl, Z is O, S, $NR^\delta$ or $SiR^\delta R^\epsilon$, where $R^\delta$ and $R^\epsilon$ are each, independently of one another, hydrogen, alkyl, cycloalkyl, heterocycloalkyl, aryl or hetaryl, or Z is a $C_1$-$C_4$-alkylene bridge which may have a double bond and/or bear an alkyl, cycloalkyl, heterocycloalkyl, aryl or hetaryl substituent, or Z is a $C_2$-$C_4$-alkylene bridge which is interrupted by O, S or $NR^\delta$ or $SiR^\delta R^\epsilon$, where, in the groups of the formulae IV.a and IV.b, two adjacent radicals $R^I$ to $R^{VI}$ together with the carbon atoms of the benzene ring to which they are bound may also form a fused ring system having 1, 2 or 3 further rings, where, in the groups of the formulae IV.h to IV.n, two geminal radicals $R^I$, $R^{I'}$; $R^{II}$, $R^{II'}$; $R^{III}$, $R^{III'}$ and/or $R^{IV}$, $R^{IV'}$ may also represent oxo or a ketal thereof, $A^1$ and $A^2$ are each, independently of one another, O, S, $SiR^\phi R^\gamma$, $NR^\eta$ or $CR^\iota R^\kappa$, where $R^\phi$, $R^\gamma$, $R^\eta$, $R^\iota$ and $R^\kappa$ are each, independently of one another, hydrogen, alkyl, cycloalkyl, heterocycloalkyl, aryl or hetaryl, $A^3$ and $A^4$ are each, independently of one another, $SiR^\phi$, N or $CR^\iota$, D is a divalent bridging group of the formula

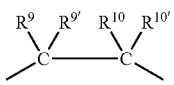

where
$R^9$, $R^{9'}$, $R^{10}$ and $R^{10'}$ are each, independently of one another, hydrogen, alkyl, cycloalkyl, aryl, halogen, trifluoromethyl, carboxyl, carboxylate or cyano,
where $R^{9'}$ together with $R^{10'}$ can also represent the second bond of a double bond between the two carbon atoms to which $R^{9'}$ and $R^{10'}$ are bound, and/or $R^9$ and $R^{10}$ together with the carbon atoms to which they are bound may also form a 4- to 8-membered carbocycle or heterocycle which may additionally be fused with one, two or three cycloalkyl, heterocycloalkyl, aryl or hetaryl groups, where the heterocycle and, if present, the fused-on groups may each bear, independently of one another, one, two, three or four substituents selected from among alkyl, cycloalkyl, heterocycloalkyl, aryl, hetaryl, $COOR^f$, $COO^-M^+$, $SO_3R^f$, $SO_3^-M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^eCH_2O)_yR^f$, $(CH_2N(E^4))_yR^f$, $(CH_2CH_2N(E^4))_yR^f$, halogen, trifluoromethyl, nitro, acyl and cyano, where $R^f$, $E^4$, $E^5$ and $E^6$ are identical or different radicals selected from among hydrogen, alkyl, cycloalkyl and aryl, $R^e$ is hydrogen, methyl or ethyl, $M^+$ is a cation, $X^-$ is an anion and y is an integer from 1 to 240.

Preference is given to the bridging group Y being a group of the formula IV.a in which the groups $A^1$ and $A^2$ are selected from among the groups O, S and $CR^iR^k$, in particular from among O, S, the methylene group ($R^i=R^k=H$), the dimethylmethylene group ($R^i=R^k=CH_3$), the diethylmethylene group ($R^i=R^k=C_2H_5$), the di-n-propylmethylene group ($R^i=R^k=$n-propyl) or the di-n-butylmethylene group ($R^d=R^e=$n-butyl). Particular preference is given to bridging groups Y in which $A^1$ is different from $A^2$, with $A^1$ preferably being a $CR^iR^k$ group and $A^2$ preferably being an O or S group, particularly preferably an oxa group O.

Preference is given to the bridging group Y being a group of the formula IV.b in which D is a divalent bridging group selected from among the groups

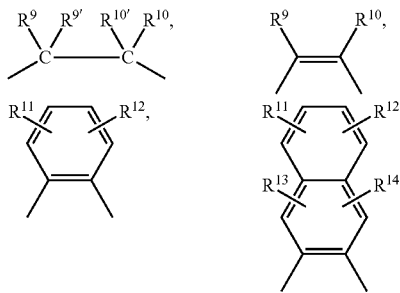

where $R^9$, $R^{9'}$, $R^{10}$ and $R^{10'}$ are each, independently of one another, hydrogen, alkyl, cycloalkyl, aryl, halogen, trifluoromethyl, carboxyl, carboxylate or cyano or are joined to one another to form a $C_3$-$C_4$-alkylene group and $R^{11}$, $R^{12}$, $R^{13}$ and $R^{14}$ can each be, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, aryl or nitro. Preference is given to the groups $R^9$, $R^{9'}$, $R^{10}$ and $R^{10'}$ each being hydrogen, $C_1$-$C_{10}$-alkyl or carboxylate and the groups $R^{11}$, $R^{12}$, $R^{13}$ and $R^{14}$ each being hydrogen, $C_1$-$C_{10}$-alkyl, halogen, in particular fluorine, chlorine or bromine, trifluoromethyl, $C_1$-$C_4$-alkoxy, carboxylate, sulfonate or $C_1$-$C_8$-aryl. $R^9$, $R^{9'}$, $R^{10}$, $R^{10'}$, $R^{11}$, $R^{12}$, $R^{13}$ and $R^{14}$ are particularly preferably each hydrogen. For use in an aqueous reaction medium, preference is given to chelating pnicogen compounds in which 1, 2 or 3, preferably 1 or 2, in particular 1, of the groups $R^{11}$, $R^{12}$, $R^{13}$ and/or $R^{14}$ are a $COO^-M^+$, $SO_3^-M^+$or $(NE^1E^2E^3)^+X^-$group, where $M^+$ and $X^-$ are as defined above.

Particularly preferred bridging groups D are the ethylene group

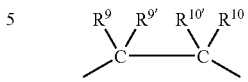

and the 1,2-phenylene group

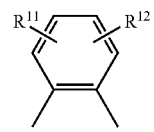

In the bridging groups Y of the formulae IV.a and IV.b, the substituents $R^I$, $R^{II}$, $R^{III}$, $R^{IV}$, $R^V$ and $R^{VI}$ are preferably selected from among hydrogen, alkyl, alkoxy, cycloalkyl, heterocycloalkyl, aryl and hetaryl. In a first preferred embodiment, $R^I$, $R^{II}$, $R^{III}$, $R^{IV}$, $R^V$ and $R^{VI}$ are each hydrogen. In a further preferred embodiment, $R^I$ and $R^V$ are each, independently of one another, $C_1$-$C_4$-alkyl or $C_1$-$C_4$-alkoxy. $R^I$ and $R^{VI}$ are preferably selected from among methyl, ethyl, isopropyl, tert-butyl and methoxy. In these compounds, $R^{II}$, $R^{III}$, $R^{IV}$ and $R^V$ are preferably each hydrogen. In a further preferred embodiment, $R^{II}$ and $R^V$ are each, independently of one another, $C_1$-$C_4$-alkyl or $C_1$-$C_4$-alkoxy. $R^{II}$ and $R^V$ are preferably selected from among methyl, ethyl, isopropyl and tert-butyl. In these compounds, $R^I$, $R^{III}$, $R^{IV}$ and $R^{VI}$ are preferably each hydrogen.

When two adjacent radicals selected from among $R^I$, $R^{II}$, $R^{III}$, $R^{IV}$, $R^V$ and $R^{VI}$ in the bridging groups Y of the formulae IV.a and IV.b form a fused-on ring system, this is preferably a benzene ring or naphthalene unit. Fused-on benzene rings are preferably unsubstituted or have 1, 2 or 3, in particular 1 or 2, substituents selected from among alkyl, alkoxy, halogen, $SO_3H$, sulfonate, $NE^1E^2$, alkylene-$NE^1E^2$, trifluoromethyl, nitro, $COOR^f$, alkoxycarbonyl, acyl and cyano. Fused-on naphthalene units are preferably unsubstituted or have a total of 1, 2 or 3, in particular 1 or 2, of the substituents mentioned above in the case of the fused-on benzene rings in the ring which is not fused on and/or in the fused-on ring.

Preference is given to Y being a group of the formula IV.c in which $R^{IV}$ and $R^V$ are each, independently of one another, $C_1$-$C_4$-alkyl or $C_1$-$C_4$-alkoxy. $R^{IV}$ and $R^V$ are preferably selected from among methyl, ethyl, isopropyl, tert-butyl and methoxy. In these compounds $R^I$, $R^{II}$, $R^{III}$, $R^{VI}$, $R^{VII}$ and $R^{VIII}$ are preferably each hydrogen.

Preference is also given to Y being a group of the formula IV.c in which $R^I$ and $R^{VIII}$ are each, independently of one another, $C_1$-$C_4$-alkyl or $C_1$-$C_4$-alkoxy. $R^I$ and $R^{VIII}$ are particularly preferably each tert-butyl. In these compounds, $R^{II}$, $R^{III}$, $R^{IV}$, $R^V$, $R^{VI}$, $R^{VII}$ are particularly preferably each hydrogen. Preference is also given to $R^{III}$ and $R^{VI}$ in these compounds each being, independently of one another, $C_1$-$C_4$-alkyl or $C_1$-$C_4$-alkoxy. $R^{III}$ and $R^{VI}$ are particularly preferably selected independently from among methyl, ethyl, isopropyl, tert-butyl and methoxy.

Preference is also given to Y being a group of the formula IV.c in which $R^{II}$ and $R^{VII}$ are each hydrogen. In these compounds $R^I$, $R^{III}$, $R^{IV}$, $R^V$, $R^{VI}$ and $R^{VIII}$ are preferably each, independently of one another, $C_1$-$C_4$-alkyl or $C_1$-$C_4$-alkoxy. $R^I$, $R^{III}$, $R^{IV}$, $R^V$, $R^{VI}$ and $R^{VIII}$ are particularly preferably selected independently from among methyl, ethyl, isopropyl, tert-butyl and methoxy.

Furthermore, preference is given to Y being a group of the formula IV.d in which Z is a $C_1$-$C_4$-alkylene group, in particular methylene. In these compounds, $R^{IV}$ and $R^V$ are preferably each, independently of one another, $C_1$-$C_4$-alkyl or $C_1$-$C_4$-alkoxy. $R^{IV}$ and $R^V$ are particularly preferably selected independently from among methyl, ethyl, isopropyl, tert-butyl and methoxy. The radicals $R^I$, $R^{II}$, $R^{III}$, $R^{VI}$, $R^{VII}$ and $R^{VIII}$ are preferably each hydrogen.

Preference is also given to Y being a group of the formula IV.d in which Z is a $C_1$-$C_4$-alkylene bridge bearing at least one alkyl, cycloalkyl or aryl radical. Z is particularly preferably a methylene bridge bearing two $C_1$-$C_4$-alkyl radicals, in particular two methyl radicals. In these compounds, the radicals $R^I$ and $R^{VIII}$ are preferably each, independently of one another, $C_1$-$C_4$-alkyl or $C_1$-$C_4$-alkoxy. $R^I$ and $R^{VIII}$ are particularly preferably selected independently from among methyl, ethyl, isopropyl, tert-butyl and methoxy.

Furthermore, preference is given to Y being a group of the formula IV.e in which $R^I$ and $R^{XII}$ are each, independently of one another, $C_1$-$C_4$-alkyl or $C_1$-$C_4$-alkoxy. In particular, $R^I$ and $R^{XII}$ are selected independently from among methyl, ethyl, isopropyl, tert-butyl, methoxy and alkoxycarbonyl, preferably methoxycarbonyl. In these compounds, the radicals $R^{II}$ to $R^{XI}$ are particularly preferably each hydrogen.

Preference is also given to Y being a group of the formula IV.f in which $R^I$ and $R^{XII}$ are each, independently of one another, $C_1$-$C_4$-alkyl or $C_1$-$C_4$-alkoxy. In particular, $R^I$ and $R^{XII}$ are selected independently from among methyl, ethyl, isopropyl, tert-butyl and methoxy. In these compounds, the radicals $R^{II}$ to $R^{XI}$ are particularly preferably each hydrogen.

Furthermore, preference is given to Y being a group of the formula IV.g in which Z is a $C_1$-$C_4$-alkylene group bearing at least one alkyl, cycloalkyl or aryl substituent. Z is particularly preferably a methylene group bearing two $C_1$-$C_4$-alkyl radicals, especially two methyl radicals. In these compounds, the radicals $R^I$ and $R^{VIII}$ are particularly preferably each, independently of one another, $C_1$-$C_4$-alkyl or $C_1$-$C_4$-alkoxy. In particular, $R^I$ and $R^{VIII}$ are selected independently from among methyl, ethyl, isopropyl, tert-butyl and methoxy. The radicals $R^{II}$, $R^{III}$, $R^{IV}$, $R^V$, $R^{VI}$ and $R^{VII}$ are preferably each hydrogen.

Preference is also given to Y being a group of the formula IV.h in which $R^I$, $R^{I'}$, $R^{II}$, $R^{II'}$, $R^{III}$ and $R^{III'}$ are each hydrogen.

Preference is also given to Y being a group of the formula IV.h in which $R^{II}$ and $R^{II'}$ together represent an oxo group or a ketal thereof and the other radicals are each hydrogen.

Preference is also given to Y being a group of the formula IV.i in which $R^I$, $R^{I'}$, $R^{II}$, $R^{II'}$, $R^{III}$ and $R^{III'}$ are each hydrogen.

Preference is also given to Y being a group of the formula IV.i in which $R^{II}$ and $R^{II'}$ together represent an oxo group or a ketal thereof and the other radicals are each hydrogen.

Preference is also given to Y being a group of the formula IV.k in which $R^I$, $R^{I'}$, $R^{II}$, $R^{II'}$, $R^{III}$, $R^{III'}$, $R^{IV}$ and $R^{IV'}$ are each hydrogen.

Preference is also given to Y being a group of the formula IV.l in which $R^I$, $R^{I'}$, $R^{II}$, $R^{II'}$, $R^{III}$, $R^{III'}$, $R^{IV}$ and $R^{IV'}$ are each hydrogen.

Preference is also given to Y being a group of the formula IV.m in which $R^I$, $R^{I'}$, $R^{II}$, $R^{II'}$, $R^{III}$, $R^{III'}$, $R^{IV}$ and $R^{IV'}$ are each hydrogen.

Preference is also given to Y being a group of the formula IV.n in which $R^I$, $R^{I'}$, $R^{II}$, $R^{II'}$, $R^{III}$, $R^{III'}$, $R^{IV}$ and $R^{IV'}$ are each hydrogen.

Preference is also given to Y being a group of the formula IV.o in which $R^I$, $R^{I'}$, $R^{II}$, $R^{II'}$, $R^{III}$, $R^{III'}$, $R^{IV}$ and $R^{IV'}$ are each hydrogen.

Preference is also given to Y being a group of the formula IV.o in which one of the radicals $R^I$ to $R^{IV}$ is $C_1$-$C_4$-alkyl or $C_1$-$C_4$-alkoxy. Particular preference is then given to at least one of the radicals $R^I$ to $R^{IV}$ being methyl, ethyl, isopropyl, tert-butyl or methoxy.

Preference is also given to Y being a group of the formula IV.p in which $R^I$, $R^{II}$, $R^{III}$ and $R^{IV}$ are each hydrogen.

Preference is also given to Y being a group of the formula IV.p in which one of the radicals $R^I$, $R^{II}$, $R^{III}$ or $R^{IV}$ is $C_1$-$C_4$-alkyl or $C_1$-$C_4$-alkoxy. Particular preference is then given to one of the radicals $R^I$ to $R^{IV}$ being methyl, ethyl, tert-butyl or methoxy.

Preference is also given to Y being a group of the formula IV.q in which $R^I$ and $R^{VI}$ are each, independently of one another, $C_1$-$C_4$-alkyl or $C_1$-$C_4$-alkoxy. $R^I$ and $R^{VI}$ are particularly preferably selected independently from among methyl, ethyl, isopropyl, tert-butyl and methoxy. In these compounds, $R^{II}$, $R^{III}$, $R^{IV}$ and $R^V$ are particularly preferably each hydrogen. Preference is also given to $R^I$, $R^{III}$, $R^{IV}$ and $R^{VI}$ in the compounds IV.q each being, independently of one another, $C_1$-$C_4$-alkyl or $C_1$-$C_4$-alkoxy. Particular preference is then given to $R^I$, $R^{III}$, $R^{IV}$ and $R^{VI}$ being selected independently from among methyl, ethyl, isopropyl, tert-butyl and methoxy.

Preference is also given to Y being a group of the formula IV.r in which $R^I$ and $R^{VI}$ are each, independently of one another, $C_1$-$C_4$-alkyl or $C_1$-$C_4$-alkoxy. $R^I$ and $R^{VI}$ are particularly preferably selected independently from among methyl, ethyl, isopropyl, tert-butyl and methoxy. In these compounds, $R^{II}$, $R^{III}$, $R^{IV}$ and $R^V$ are particularly preferably each hydrogen. Preference is also given to $R^{III}$ and $R^{IV}$ in these compounds each being, independently of one another, $C_1$-$C_4$-alkyl or $C_1$-$C_4$-alkoxy. Particular preference is then given to $R^{III}$ and $R^{IV}$ being selected independently from among methyl, ethyl, isopropyl, tert-butyl and methoxy.

Preference is also given to Y being a group of the formula IV.s, IV.t or IV.u in which Z is $CH_2$, $C_2H_2$ or $C_2H_4$.

In the compounds of the formulae IV.s, IV.t and IV.u, the indicated bonds to the bridged groups can equally well be in the endo and exo positions.

The catalysts used according to the invention can further comprise at least one additional ligand which is preferably selected from among halides, amines, carboxylates, acetylacetonate, arylsulfonates and alkylsulfonates, hydride, CO, olefins, dienes, cycloolefins, nitriles, N-containing heterocycles, aromatics and heteroaromatics, ethers, $PF_3$, phospholes, phosphabenzenes, monodentate, bidentate and polydentate phosphine, phosphinite, phosphonite, phosphite ligands and mixtures thereof.

In general, the catalysts or catalyst precursors used in each case are converted under hydroformylation conditions into catalytically active species of the formula $H_tM_u(CO)_vL_w$, where M is a metal of transition group VIII, L is a phosphoramidite compound and t, u, v, w are integers which depend on the valence and type of the metal and on the number of coordination sites occupied by the ligand L. It is preferred that v and w each have, independently of one another, a value of at least 1, e.g. 1, 2 or 3. The sum of v and w is preferably from 1 to 5. If desired, the complexes may further comprise at least one of the above-described additional ligands.

In a preferred embodiment, the hydroformylation catalysts are prepared in situ in the reactor used for the hydroformylation reaction. However, the catalysts used according to the invention can, if desired, also be prepared separately and isolated by customary methods. For the in-situ preparation of the catalysts used according to the invention, it is possible, for example, to react at least one phosphoramidite compound, a compound or a complex of a metal of transition group VIII, if appropriate at least one further additional ligand and, if appropriate, an activating agent in an inert solvent under the hydroformylation conditions.

Suitable rhodium compounds or complexes are, for example, rhodium(II) and rhodium(III) salts such as rhodium (II) chloride, rhodium(III) nitrate, rhodium(III) sulfate, potassium rhodium sulfate, rhodium(II) or rhodium(III) carboxylate, rhodium(II) and rhodium(III) acetate, rhodium(II) and rhodium(III) ethylhexanoate, rhodium(III) oxide, salts of rhodic(III) acid, trisammonium hexachlororhodate(III), etc. Also suitable are rhodium complexes such as dicarbonylrhodium acetylacetonate, acetylacetonato-bisethylenerhodium(I), etc. Preference is given to using dicarbonylrhodium acetylacetonate or rhodium acetate.

Likewise suitable are ruthenium salts or compounds. Suitable ruthenium salts are, for example, ruthenium(III) chloride, ruthenium(IV), ruthenium(VI) or ruthenium(VIII) oxide, alkali metal salts of ruthenium oxo acids such as $K_2RuO_4$ or $KRuO_4$ or complexes such as $RuHCl(CO)(PPh_3)_3$. It is also possible to use the metal carbonyls of ruthenium, for example dodecacarbonyltriruthenium or octadecacarbonylhexaruthenium, or mixed forms in which CO is partly replaced by ligands of the formula $PR_3$, e.g. $Ru(CO)_3(PPh_3)_2$, in the process of the invention.

Suitable cobalt compounds are, for example, cobalt(II) chloride, cobalt(II) sulfate, cobalt(II) carbonate, cobalt(II) nitrate, their amine or hydrate complexes, cobalt carboxylates, such as cobalt acetate, cobalt ethylhexanoate, cobalt naphthanoate, and also the cobalt caproate complex. Here too, the carbonyl complexes of cobalt such as octacarbonyl dicobalt, dodecacarbonyl tetracobalt and hexadecacarbonyl hexacobalt can be used.

The abovementioned and further suitable compounds of cobalt, rhodium, ruthenium and iridium are known in principle and are adequately described in the literature or can be prepared by a person skilled in the art by methods analogous to those for the known compounds.

Suitable activating agents are, for example, Bronsted acids, Lewis acids, e.g. $BF_3$, $AlCl_3$, $ZnCl_2$, $SnCl_2$ and Lewis bases.

Suitable starting olefins for the process of the invention are in principle all compounds which contain one or more ethylenically unsaturated double bonds. These include olefins having terminal or internal double bonds, straight-chain or branched olefins, cyclic olefins and also olefins which bear substituents which are essentially inert under the hydroformylation conditions. Preference is given to starting olefins comprising olefins having from 4 to 12, particularly preferably from 4 to 6, carbon atoms. The olefins used for the hydroformylation are preferably selected from among linear (straight-chain) olefins and olefin mixtures comprising at least one linear olefin. The process of the invention makes it possible to hydroformylate, in particular, linear α-olefins, linear internal olefins and mixtures of linear α-olefins and linear internal olefins.

α-Olefins preferred as substrates for the hydroformylation process of the invention are $C_4$-$C_{20}$-α-olefins, e.g. 1-butene, isobutene, 1-pentene, 2-methyl-1-butene, 1-hexene, 1-heptene, 1-octene, 1-nonene, 1-decene, 1-undecene, 1-dodecene, allyl alcohols, etc.

Preference is given to linear α-olefins and olefin mixtures comprising at least one linear α-olefin.

The unsaturated compound used for the hydroformylation is preferably selected from among internal linear olefins and olefin mixtures comprising at least one internal linear olefin. Preferred linear internal olefins are $C_4$-$C_{20}$-olefins, such as 2-butene, 2-pentene, 2-hexene, 3-hexene, 2-heptene, 3-heptene, 2-octene, 3-octene, 4-octene, etc., and mixtures thereof.

Preferred branched, internal olefins are $C_4$-$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Further olefins suitable for the hydroformylation process are $C_5$-$C_8$-cycloalkenes, such as cyclopentene, cyclohexene, cycloheptene, cyclooctene and derivatives thereof, e.g. their $C_1$-$C_{20}$-alkyl derivatives having from 1 to 5 alkyl substituents. Other olefins suitable for the hydroformylation process are vinylaromatics such as styrene, α-methylstyrene, 4-isobutylstyrene, etc. Olefins suitable for the hydroformylation process additionally include α,β-ethylenically unsaturated monocarboxylic and/or dicarboxylic acids, their esters, semiesters and amides, e.g. acrylic acid, methacrylic acid, maleic acid, fumaric acid, crotonic acid, itaconic acid, methyl 3-pentenoate, methyl 4-pentenoate, methyl oleate, methyl acrylate and methyl methacrylate. Further olefins suitable for the hydroformylation process are unsaturated nitriles, such as 3-pentenenitrile, 4-pentenenitrile and acrylonitrile. Further olefins suitable for the hydroformylation process are vinyl ethers, e.g. vinyl methyl ether, vinyl ethyl ether, vinyl propyl ether, etc. Other olefins suitable for the hydroformylation process are alkenols, alkenediols and alkadienols such as 2,7-octadien-1-ol. Further olefins suitable for the hydroformylation process are dienes or polyenes having isolated or conjugated double bonds. These include, for example, 1,3-butadiene, 1,4-pentadiene, 1,5-hexadiene, 1,6-heptadiene, 1,7-octadiene, 1,9-decadiene, vinylcyclohexene, dicyclopentadiene, 1,5,9-cyclooctatriene, homopolymers and copolymers of butadiene and also olefins having terminal and internal double bonds, e.g. 1,4-octadiene.

The hydroformylation process of the invention is preferably carried out using an industrially available olefin-containing hydrocarbon mixture.

Preferred olefin mixtures which are available on an industrial scale result from the cracking of hydrocarbons in petroleum processing, for example by catalytic cracking such as fluid catalytic cracking (FCC), thermal cracking or hydrocracking with subsequent dehydrogenation. One suitable industrial olefin mixture is a $C_4$ fraction. $C_4$ fractions can be obtained, for example, by fluid catalytic cracking or steam cracking of gas oil or by steam cracking naphtha. Depending on the composition of the $C_4$ fraction, a distinction is made between the total $C_4$ fraction (raw $C_4$ fraction), the raffinate I obtained after 1,3-butadiene has been separated off and also the raffinate II obtained after the isobutene has been separated off. A further suitable industrial olefin mixture is the $C_5$ fraction obtainable in the cracking of naphtha. Olefin-containing hydrocarbon mixtures containing compounds having from 4 to 6 carbon atoms which are suitable for use in step a) can also be obtained by catalytic dehydrogenation of suitable industrially available paraffin mixtures. Thus, for example, $C_4$ olefin mixtures can be produced from liquefied petroleum gas (LPG) and liquefied natural gas (LNG). The latter comprises, in addition to the LPG fraction, relatively large amounts of high molecular weight hydrocarbons (light naphtha) and is thus also suitable for preparing $C_5$- and $C_6$-olefin mixtures. Olefin-containing hydrocarbon mixtures comprising monoolefins having from 4 to 6 carbon atoms can be prepared from LPG or LNG streams by conventional methods known to those skilled in the art which, in addition to dehydrogenation, generally comprise one or more work-up steps. Such steps include, for example, the removal of at least part of the saturated hydrocarbons present in the abovementioned olefin feed mixtures. The saturated hydrocarbons can, for example, be reused for the preparation of starting olefins by cracking and/or dehydrogenation. However, the olefins used in the process of the invention can also contain a proportion of saturated hydrocarbons which are inert under the hydroformylation conditions of the invention. The proportion of these saturated components is generally not more than 60% by weight, preferably not more than 40% by weight, particularly preferably not more than 20% by weight, based on the total amount of olefins and saturated hydrocarbons present in the hydrocarbon starting material.

A raffinate II suitable for use in the process of the invention has, for example, the following composition:
from 0.5 to 5% by weight of isobutane,
from 5 to 20% by weight of n-butane,
from 20 to 40% by weight of trans-2-butene,
from 10 to 20% by weight of cis-2-butene,
from 25 to 55% by weight of 1-butene,
from 0.5 to 5% by weight of isobutene
and also trace gases such as 1,3-butadiene, propene, propane, cyclopropane, propadiene, methylcyclopropane, vinylacetylene, pentenes, pentanes, etc., in concentrations of not more than 1% by weight in each case.

It has surprisingly been found that catalytically active fluids based on metal complexes of phosphoramidite compounds can be additionally stabilized by bringing them into contact with a base. Thus, longer catalyst operating lives are achieved in the process of the invention than in hydroformylation processes known from the prior art which use catalysts based either on conventional monodentate and polydentate ligands or, in particular, based on phosphoramidite ligands. The catalytic activity is generally not adversely affected by contacting with the base.

The invention further provides a method of stabilizing a catalytically active fluid comprising a dissolved metal complex of a metal of transition group VIII of the Periodic Table of the Elements with at least one phosphoramidite compound as ligand in the hydroformylation of ethylenically unsaturated compounds, which comprises bringing the fluid into contact with a base.

The invention also provides for the use of bases for stabilizing a catalytically active fluid comprising a dissolved metal complex of a metal of transition group VIII of the Periodic Table of the Elements with at least one phosphoramidite compound as ligand in the hydroformylation of ethylenically unsaturated compounds.

The invention is illustrated by the following nonrestrictive examples.

EXAMPLES

1. Preparation of the Compound (1)

28.5 g (218 mmol) of 3-methylindole (skatole) together with about 50 ml of dried toluene were placed in a reaction vessel and the solvent was distilled off under reduced pressure to remove traces of water by azeotropic distillation. This procedure was repeated once more. The residue was subsequently taken up in 700 ml of dried toluene under argon and cooled to −65° C. 14.9 g (109 mmol) of PCl$_3$ followed by 40 g (396 mmol) of triethylamine were then added slowly at −65° C. The reaction mixture was brought to room temperature over a period of 16 hours and then refluxed for 16 hours. 19.3 g (58 mmol) of 4,5-dihydroxy-2,7-di-tert-butyl-9,9-dimethylxanthene in 300 ml of dried toluene were added to the reaction mixture, the mixture was then refluxed for 16 hours and, after cooling to room temperature, the colorless solid which had precipitated (triethylamine hydrochloride) was filtered off with suction, the solvent was distilled off and the residue was recrystallized twice from hot ethanol. Drying under reduced pressure gave 36.3 g (71% of theory) of a colorless solid.

$^{31}$P-NMR (298K): δ=105 ppm.

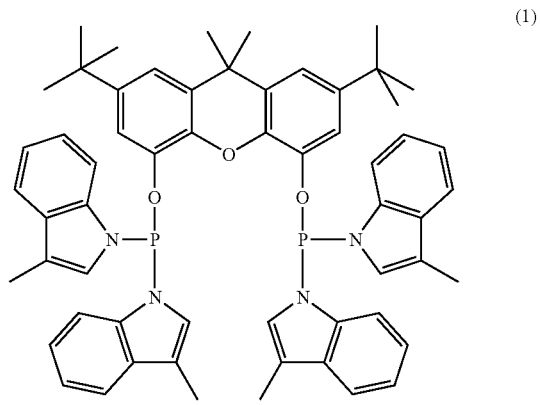

(1)

2. Hydroformylation of Trans-2-butene without Additive (Comparative Example)

0.005 g of Rh(CO)$_2$(acac) and 0.181 g of the compound (1) were dissolved in 10.17 g of xylene under a protective gas atmosphere and the mixture was transferred to a 100 ml steel autoclave. The autoclave was pressurized with 10 bar of synthesis gas (CO/H$_2$=1:2) and then heated to 90° C. over a period of one hour. The autoclave was then carefully depressurized to 7 bar at 90° C., and 10.81 g of a liquefied gas mixture (30% by volume of trans-2-butene and 70% by volume of isobutane) were injected via a lock by means of synthesis gas of the abovementioned composition (p=12 bar). The pressure was then set to 16 bar (total) by means of the synthesis gas. During the reaction time of 4 hours, the temperature was kept at 90° C. and the pressure was maintained at 16 bar (total) by addition of CO/H$_2$ (1:1). After the reaction was complete, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| | |
|---|---|
| Conversion | 32% |
| Yield | 31% |
| Proportion of n product | 93% |

3. Degradation Experiment with Addition of N,N-dimethylaniline 0.005 g of Rh(CO)$_2$(acac), 0.181 g of compound (1) and 0.26 g of N,N-dimethylaniline were dissolved in 8.12 g of Texanole® (2,2,4-trimethyl-1,3-pentanediol monobutyrate, from Eastman) under a protective gas atmosphere and the mixture was transferred to a 60 ml steel autoclave. The autoclave was pressurized at 25° C. with 20 bar of CO/H$_2$ (1:1) and heated to 120° C. over a period of 60 minutes. The autoclave was then carefully depressurized to 7 bar at 120° C. and 11.23 g of a liquefied gas mixture (2.9% by volume of isobutane; 14.6% by volume of n-butane; 27.4% by volume of trans-2-butene; 37.4% by volume of 1-butene; 2.6% by volume of isobutene; 15.3% of cis-2-butene) were injected via a lock by means of CO/H$_2$ (1:1) at 12 bar. The pressure was increased to 28 bar (total) by means of CO/H$_2$ (1:1) and the autoclave was maintained at 120° C. for 24 hours. After the end of the reaction time, the autoclave was cooled, depressurized and a sample for $^{31}$P-NMR analysis was taken under a protective gas atmosphere to determine the degree to which the ligand had been degraded.

Integration of the $^{31}$P-NMR spectrum indicated that 18% of the compound (1) had been degraded.

The mixture was subsequently returned to the autoclave, the autoclave was flushed three times with nitrogen and then maintained at 120° C. and a nitrogen pressure of 3 bar for 24 hours to simulate long-term stressing of the catalyst as occurs in prolonged continuous operation. After the end of the reaction time, the autoclave was cooled, depressurized and a sample for $^{31}$P-NMR analysis was taken under a protective gas atmosphere in order to determine the degree to which the ligand had been degraded.

Integration of the $^{31}$P-NMR spectrum indicated that a total of only 42% of the compound (1) had been degraded.

4. Hydroformylation of Trans-2-butene with Addition of N,N-dimethylaniline 0.005 g of Rh(CO)$_2$(acac), 0.181 g of the compound (1) and 0.025 g of N,N-dimethyl-aniline were dissolved in 10.17 g of xylene under a protective gas atmosphere and the mixture was transferred to a 100 ml steel autoclave. The autoclave was pressurized with 10 bar of CO/H$_2$ (1:2) and was then heated to 90° C. over a period of 1 hour. The autoclave was then carefully depressurized to 7 bar at 90° C. and 10.81 g of a liquefied gas mixture (30% by volume of trans-2-butene and 70% by volume of isobutane) were injected via a lock by means of CO/H$_2$ (1:2) at 12 bar and the pressure was set to 16 bar (total) by means of CO/H$_2$ (1:2). During the reaction time of 4 hours, the temperature was kept at 90° C. and the pressure was maintained at 16 bar (total) by means of CO/H$_2$ (1:1). After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| | |
|---|---|
| Conversion | 30% |
| Yield | 28% |
| Proportion of n product | 94% |

Conversion, yield and proportion of n product were not reduced significantly compared to comparative example 2 by addition of the base.

5. Degradation Experiment with Addition of N,N,2,4,6-pentamethylaniline 0.005 g of Rh(CO)$_2$(acac), 0.181 g of compound (1) and 0.35 g of N,N,2,4,6-penta-methylaniline were dissolved in 8.11 g of Texanol under a protective gas atmosphere and the mixture was transferred to a 60 ml steel autoclave. The autoclave was pressurized with 20 bar of CO/H$_2$ (1:1) at 25° C. and was then heated to 120° C. over a period of 60 minutes. The autoclave was then carefully depressurized to 7 bar at 120° C. and 11.23 g of a liquefied gas mixture (2.9% by volume of isobutane; 14.6% by volume of n-butane; 27.4% by volume of trans-2-butene; 37.4% by volume of 1-butene; 2.6% by volume of isobutene; 15.3% of cis-2-butene) were then injected via a lock by means of CO/H$_2$ (1:1) at 12 bar. The pressure was increased to 28 bar (total) by means of CO/H$_2$ (1:1) and the autoclave was maintained at 120° C. for 24 hours.

After the end of the reaction time, the autoclave was cooled, depressurized and a sample for $^{31}$P-NMR analysis was taken under a protective gas atmosphere to determine the degree to which the ligand had been degraded.

Integration of the $^{31}$P-NMR spectrum indicated that 4% of the compound (1) had been degraded.

The mixture was subsequently returned to the autoclave, the autoclave was flushed three times with nitrogen and then maintained at 120° C. and a nitrogen pressure of 3 bar for 24 hours. After the end of the reaction time, the autoclave was cooled, depressurized and a sample for $^{31}$P-NMR analysis was taken under a protective gas atmosphere in order to determine the degree to which the ligand had been degraded.

Integration of the $^{31}$P-NMR spectrum indicated that a total of 23% of the compound (1) had been degraded.

6. Hydroformylation of Trans-2-butene with Addition of N,N,2,4,6-pentamethylaniline 0.005 g of Rh(CO)$_2$(acac), 0.181 g of the compound (1) and 0.035 g of N,N,2,4,6-pentamethylaniline were dissolved in 10.26 g of xylene under a protective gas atmosphere and the mixture was transferred to a 100 ml steel autoclave. The autoclave was pressurized with 10 bar of CO/H$_2$ (1:2) and was then heated to 90° C. over a period of 1 hour. The autoclave was then carefully depressurized to 7 bar at 90° C. and 10.81 g of a liquefied gas mixture (30% by volume of trans-2-butene and 70% by volume of isobutane) were injected via a lock by means of CO/H$_2$ (1:2) at 12 bar and the pressure was set to 16 bar (total) by means of CO/H$_2$ (1:2). During the reaction time of 4 hours, the temperature was kept at 90° C. and the pressure was maintained at 16 bar (total) by means of CO/H$_2$ (1:1). After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| | |
|---|---|
| Conversion | 29% |
| Yield | 28% |
| Proportion of n product | 93% |

7. Hydroformylation of Trans-2-butene with Addition of 3-methylindole 0.005 g of Rh(CO)$_2$(acac), 0.180 g of the compound (1) and 0.10 g of 3-methylindole were dissolved in 10.14 g of xylene under a protective gas atmosphere and the mixture was transferred to a 100 ml steel autoclave. The autoclave was pressurized with 10 bar of CO/H$_2$ (1:2) and was then heated to 90° C. over a period of 1 hour. The autoclave was then carefully depressurized to 7 bar at 90° C. and 10.81 g of a liquefied gas mixture (30% by volume of trans-2-butene and 70% by volume of isobutane) were injected via a lock by means of CO/H$_2$ (1:2) at 12 bar and the pressure was set to 16 bar (total) by means of CO/H$_2$ (1:2). During the reaction time of 4 hours, the temperature was kept at 90° C. and the pressure was maintained at 16 bar (total) by means of CO/H$_2$ (1:1). After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| Conversion | 33% |
|---|---|
| Yield | 32% |
| Proportion of n product | 94% |

8. Hydroformylation of Trans-2-butene with Addition of Quinoline 0.005 g of Rh(CO)$_2$(acac), 0.181 g of the compound (1) and 0.029 g of quinoline were dissolved in 10.16 g of xylene under a protective gas atmosphere and the mixture was transferred to a 100 ml steel autoclave. The autoclave was pressurized with 10 bar of CO/H$_2$ (1:2) and was then heated to 90° C. over a period of 1 hour. The autoclave was then carefully depressurized to 7 bar at 90° C. and 10.81 g of a liquefied gas mixture (30% by volume of trans-2-butene and 70% by volume of isobutane) were injected via a lock by means of CO/H$_2$ (1:2) at 12 bar and the pressure was set to 16 bar (total) by means of CO/H$_2$ (1:2). During the reaction time of 4 hours, the temperature was kept at 90° C. and the pressure was maintained at 16 bar (total) by means of CO/H$_2$ (1:1). After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| Conversion | 29% |
|---|---|
| Yield | 27% |
| Proportion of n product | 90% |

9. Hydroformylation of Raffinate II without Additive (Comparative Example)

0.006 g of Rh(CO)$_2$(acac) and 0.217 g of the compound (1) were dissolved in 10.0 g of toluene under a protective gas atmosphere and the mixture was transferred to a 100 ml steel autoclave. The autoclave was pressurized with 10 bar of CO/H$_2$ (1:2) and was then heated to 90° C. over a period of 0.5 hour. The autoclave was then carefully depressurized to 7 bar at 90° C. and 10.2 g of a liquefied gas mixture (1.7% of isobutane, 12.4% of n-butane, 31.7% of trans-2-butene, 35.1% of 1-butene, 2.4% of isobutene, 16.8% of cis-2-butene) were injected via a lock by means of CO/H$_2$ (1:2) at 12 bar and the pressure was set to 17 bar (total) by means of CO/H$_2$ (1:2). During the reaction time of 4 hours, the temperature was kept at 90° C. and the pressure was maintained at 17 bar (total) by means of CO/H$_2$ (1:1). After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| Conversion | 89% |
|---|---|
| Yield | 88% |
| Proportion of n product | 95% |

10. Hydroformylation of Raffinate II with Addition of 1-H-benzotriazole 0.006 g of Rh(CO)$_2$(acac) and 0.212 g of the compound (1) and 0.014 g of 1-H-benzotriazole were dissolved in 10.1 g of toluene under a protective gas atmosphere and the mixture was transferred to a 100 ml steel autoclave. The autoclave was pressurized with 10 bar of CO/H$_2$ (1:2) and was then heated to 90° C. over a period of 0.5 hour. The autoclave was then carefully depressurized to 7 bar at 90° C. and 10.4 g of a liquefied gas mixture (1.7% of isobutane, 12.4% of n-butane, 31.7% of trans-2-butene, 35.1% of 1-butene, 2.4% of isobutene, 16.8% of cis-2-butene) were injected via a lock by means of CO/H$_2$ (1:2) at 12 bar and the pressure was set to 17 bar (total) by means of CO/H$_2$ (1:2). During the reaction time of 4 hours, the temperature was kept at 90° C. and the pressure was maintained at 17 bar (total) by means of CO/H$_2$ (1:1). After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| Conversion | 88% |
|---|---|
| Yield | 87% |
| Proportion of n product | 95% |

(no significant change compared to comparative example 9)

11. Degradation Experiment Using 1-H-benzotriazole 0.005 g of Rh(CO)$_2$(acac), 0.181 g of compound (1) and 0.024 g of 1-H-benzotriazole were dissolved in 8.02 g of Texanole® under a protective gas atmosphere and the mixture was transferred to a 60 ml steel autoclave. The autoclave was pressurized at 25° C. with 20 bar of CO/H$_2$ (1:1) and then heated to 120° C. over a period of 60 minutes. The autoclave was then carefully depressurized to 7 bar at 120° C. and 11.23 g of a liquefied gas mixture (2.9% by volume of isobutane; 14.6% by volume of n-butane; 27.4% by volume of trans-2-butene; 37.4% by volume of 1-butene; 2.6% by volume of isobutene; 15.3% of cis-2-butene) were injected via a lock by means of CO/H$_2$ (1:1) at 12 bar. The pressure was increased to 28 bar (total) by means of CO/H$_2$ (1:1) and the autoclave was maintained at 120° C. for 24 hours. After the end of the reaction time, the autoclave was cooled, depressurized and a sample for $^{31}$P-NMR analysis was taken under a protective gas atmosphere to determine the degree to which the ligand had been degraded.

Integration of the $^{31}$P-NMR spectrum indicated that 3% of the compound (1) had been degraded.

The mixture was subsequently returned to the autoclave, the autoclave was flushed three times with nitrogen and then maintained at 120° C. and a nitrogen pressure of 3 bar for 24 hours. After the end of the reaction time, the autoclave was cooled, depressurized and a sample for $^{31}$P-NMR analysis was taken under a protective gas atmosphere in order to determine the degree to which the ligand had been degraded.

Integration of the $^{31}$P-NMR spectrum indicated that a total of 29% of the compound (1) had been degraded.

12. Hydroformylation of Raffinate II and Treatment of the Reaction Product Mixture with an Ion Exchanger 0.0051 g of Rh(CO)$_2$(acac) (acac =acetylacetonate) and 0.1806 g of ligand (1) were dissolved in 8.05 g of toluene under N$_2$. This solution was analyzed by $^{31}$P-NMR (see table 1; blank) and the mixture was transferred to a 100 ml steel autoclave. The autoclave was pressurized with 20 bar of CO/H$_2$ (1:1) at 25° C., and then heated to 120° C. and maintained at this temperature for 30 minutes. The autoclave was subsequently depressurized to 7 bar and 11.37 g of liquefied gas mixture were injected via a lock by means of CO/H$_2$ (1:1) at 12 bar.

The liquefied gas mixture had the following composition (in % by weight):

| | |
|---|---|
| isobutane | 2.9% |
| n-butane | 14.6% |
| trans-2-butene | 27.4% |
| 1-butene | 37.4% |
| isobutene | 2.6% |
| cis-2-butene | 15.3% |

The pressure in the autoclave was brought to a total pressure of 28 bar by means of CO/H$_2$ (1:1) and these conditions were maintained for 24 hours. The autoclave was subsequently cooled, depressurized and a sample of the contents of the reactor were analyzed by $^{31}$P-NMR (see table 1). 21.8 g of a yellow, homogeneous solution were obtained.

The product mixture was stirred with 2 g of Amberlite® IRA 67 at 25° C. under N$_2$ for 30 minutes.

A sample of the liquid reaction mixture was subsequently analyzed by $^{31}$P-NMR (see table 1).

TABLE 1

Results of the $^{31}$P-NMR analysis:
Quantitative $^{31}$P-NMR analysis
Evaluation of the integrals in % by area

| Sample | Ligand (1) | Oxide (2) | Oxide (3) | Degradation products |
|---|---|---|---|---|
| Blank | 98.6 | | 1.4 | |
| After hydroformylation | 25.3 | 7.1 | 1.5 | 66.1 |
| After treatment with ion exchanger | 37.3 | 10.2 | 3.1 | 49.4 |

The oxidation is caused by sampling. The oxides are to be counted as ligand:

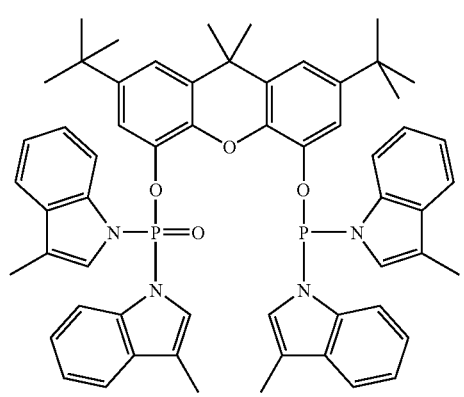

(2)

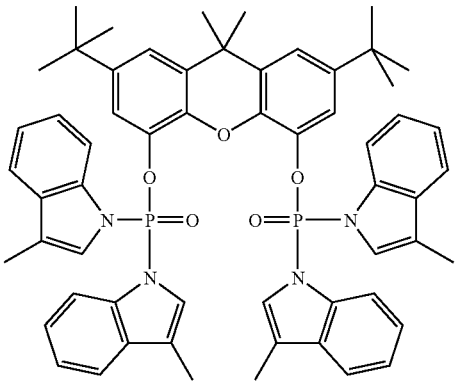

(3)

13. Continuous Hydroformylation without Stabilization (Comparative Example)

FIG. 1 shows a miniplant for carrying out continuous hydroformylations. This consists of two autoclaves with lifting stirrer connected in series (1 and 2) and having a liquid capacity of 0.4 l (reactor 1) and 1.9 l (reactor 2), a pressure separator (3), a flash stripping column (4) operated using nitrogen as stripping gas for separating off the catalyst-containing high-boiling phase from the product phase and unreacted C$_4$-hydrocarbons and also an ion exchanger bed (5). In this plant, raffinate II (isobutane 2.4%, n-butane 12.6%, trans-2-butene 31.5%, 1-butene 36.8%, isobutene 1.8%, cis-2-butene 14.9%) was hydroformylated using rhodium and the ligand from example 1 as catalyst. The catalyst recycle stream from the flash column (4) amounted to about 200 g/h and the raffinate II inflow was about 180 g/h. The temperature of the two reactors was 90° C. The first reactor was operated using synthesis gas having a CO:H$_2$ molar ratio of 4:6 and at a total pressure of about 17 bar. Hydrogen was additionally introduced into the second reactor and the reactor was operated at a total pressure of 16 bar. The CO content of the offgas was set to 10%. In steady-state operation over a representative period of eight days, the plant gave an aldehyde yield of 55%. The ion exchanger (5) was not active in this experiment. The rhodium concentration in the catalyst recycle stream from the flash column (4) was about 320 ppm. According to HPLC analysis, 15 000 ppm of skatOX ligand (1) were present in the catalyst recycle stream at the beginning of the period of time under consideration. After six days, only 3100 ppm of skatOX ligand (1) could be detected by HPLC analysis, and after eight days no skatOX ligand (1) could be detected.

14. Continuous Hydroformylation with Stabilization by Means of an Ion Exchanger

Figure 2:
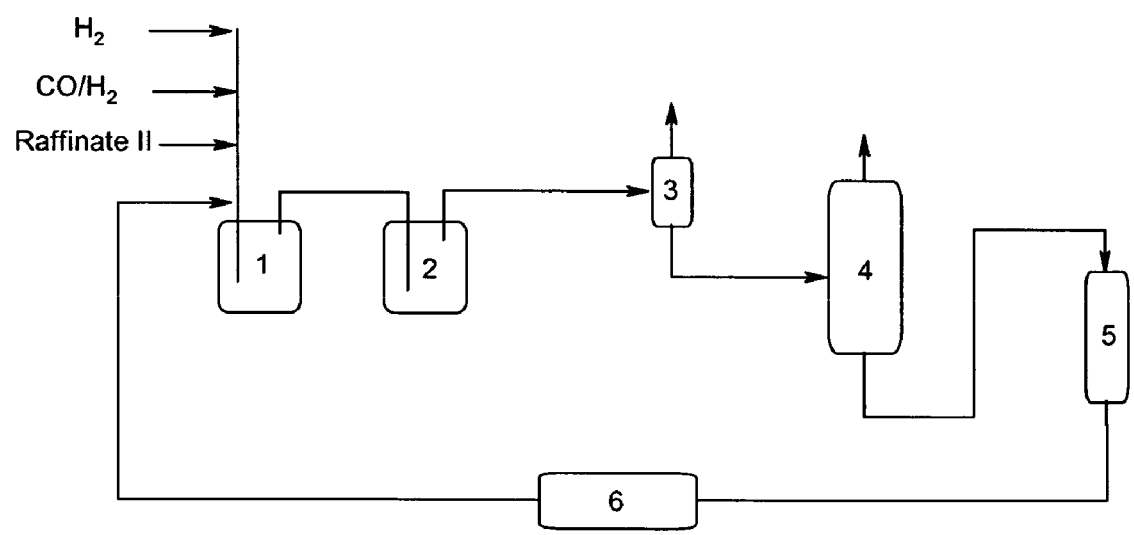
FIG. 2 shows a miniplant for carrying out continuous hydroformylations. This consists of two autoclaves with lifting stirrer connected in series (1 and 2), a pressure separator (3), a heated depressurization vessel for separating off $C_4$-hydrocarbons (4), a wiped film evaporator (5), and an ion exchanger bed (6).

FIG. 2 shows a miniplant for carrying out continuous hydroformylations. This consists of two autoclaves with lifting stirrer connected in series (1 and 2) and each having a liquid capacity of 1.9 l, a pressure separator (3), a heated depressurization vessel for separating off C$_4$-hydrocarbons (4), a wiped film evaporator (5) for separating off the catalyst-containing high-boiling phase from the product phase and an ion exchanger bed (6). In this plant, raffinate II (isobutane 3.6%, n-butane 13.8%, trans-2-butene 30.9%, 1-butene 32.0%, isobutene 2.2%, cis-2-butene 17.5%) was hydroformylated using rhodium and the ligand (1) as catalyst. The catalyst recycle stream from the distillation (5) amounted to about 250 g/h and the raffinate II inflow was about 180 g/h. The temperature of the two reactors was 90° C. The reactors were supplied with synthesis gas having a CO:H$_2$ molar ratio of 4:6 and operated at a total pressure of about 17 bar. In addition, hydrogen was introduced into the first reactor to set the CO content of the offgas to 10%. In steady-state operation over a representative period of 40 days, the plant gave an aldehyde yield of 65%. The rhodium concentration in the stream from the separator (4) to the distillation (5) was about 110 ppm. According to HPLC analysis, 7740 ppm of skatOX ligand (1) were present in the stream from the separator (4) to the distillation (5) at the beginning of the period of time under consideration. After 40 days, only 2150 ppm of (1) could be detected.

15. Hydroformylation of Raffinate II with Addition of Bottoms from a Plant 0.004 g of $Rh(CO)_2(acac)$, 0.141 g of compound (1) and 3.71 g of catalyst-containing bottoms from a continuously operated miniplant (as described in example 13) were dissolved in 5.8 g of toluene under a protective gas atmosphere and the mixture was transferred to a 100 ml steel autoclave.

The bottoms came from the miniplant described in examples 13 and 14 and contained 480 ppm of rhodium and 3800 ppm of phosphorus. The autoclave was pressurized with 10 bar of $CO/H_2$ (1:2) at 25° C. and was then heated to 90° C. over a period of 30 minutes. The autoclave was then carefully depressurized at 90° C. and 11.6 g of a liquefied gas mixture (2.9% by volume of isobutane; 14.6% by volume of n-butane; 27.4% by volume of trans-2-butene; 37.4% by volume of 1-butene; 2.6% by volume of isobutene; 15.3% of cis-2-butene) were injected via a lock by means of $CO/H_2$ (1:1) at 8 bar. The pressure was increased to 17 bar (total) by means of $CO/H_2$ (1:1) and the autoclave was maintained at 90° C. for 6 hours. After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| | |
|---|---|
| Conversion | 65% |
| Yield | 59% |
| Proportion of n product | 90.7% |

16. Hydroformylation of Raffinate II with Addition of Bottoms from a Plant Washing with Water 0.004 g of $Rh(CO)_2(acac)$, 0.130 g of compound (1) and 5.37 g of catalyst-containing bottoms from a continuously operated miniplant (as described in example 13) were dissolved in 5.37 g of toluene under a protective gas atmosphere and the mixture was transferred to a 100 ml steel autoclave.

The bottoms came from the miniplant described in examples 13 and 14 and contained 480 ppm of rhodium and 3800 ppm of phosphorus. The bottoms were shaken with water under a protective gas atmosphere before use in the experiment. The autoclave was pressurized with 10 bar of $CO/H_2$ (1:2) at 25° C. and was then heated to 90° C. over a period of 30 minutes. The autoclave was then carefully depressurized at 90° C. and 9.8 g of a liquefied gas mixture (2.9% by volume of isobutane; 14.6% by volume of n-butane; 27.4% by volume of trans-2-butene; 37.4% by volume of 1-butene; 2.6% by volume of isobutene; 15.3% of cis-2-butene) were injected via a lock by means of $CO/H_2$ (1:1) at 8 bar. The pressure was increased to 17 bar (total) by means of $CO/H_2$ (1:1) and the autoclave was maintained at 90° C. for 6 hours. After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| | |
|---|---|
| Conversion | 66% |
| Yield | 60% |
| Proportion of n product | 90.8% |

17. Hydroformylation of Raffinate II with Addition of Bottoms from a Plant Washing with Aqueous $NaHCO_3$ Solution 0.003 g of $Rh(CO)_2(acac)$, 0.104 g of compound (1) and 2.73 g of catalyst-containing bottoms from a continuously operated miniplant (as described in example 13) were dissolved in 4.27 g of toluene under a protective gas atmosphere and the mixture was transferred to a 100 ml steel autoclave.

The bottoms came from the miniplant described in examples 13 and 14 and contained 480 ppm of rhodium and 3800 ppm of phosphorus. The bottoms were shaken with aqueous $NaHCO_3$ solution under a protective gas atmosphere before use in the experiment. The autoclave was pressurized with 10 bar of $CO/H_2$ (1:2) at 25° C. and was then heated to 90° C. over a period of 30 minutes. The autoclave was then carefully depressurized at 90° C. and 10.6 g of a liquefied gas mixture (2.9% by volume of isobutane; 14.6% by volume of n-butane; 27.4% by volume of trans-2-butene; 37.4% by volume of 1-butene; 2.6% by volume of isobutene; 15.3% of cis-2-butene) were injected via a lock by means of $CO/H_2$ (1:1) at 8 bar. The pressure was increased to 17 bar (total) by means of $CO/H_2$ (1:1) and the autoclave was maintained at 90° C. for 6 hours. After the end of the reaction, the autoclave was depressurized via a cold trap and the contents of the autoclave and of the cold trap were analyzed by gas chromatography in order to determine the conversion, the yield of pentanals and the proportion of n-valeraldehyde among the pentanals.

Results of the analysis by gas chromatography:

| | |
|---|---|
| Conversion | 68% |
| Yield | 62% |
| Proportion of n product | 91.7% |

The invention claimed is:

1. A process for the hydroformylation of compounds which comprises, providing at least one compound with an ethylenically unsaturated double bond and reacting the at least one compound with carbon monoxide and hydrogen in at least one reaction zone in the presence of a catalytically active fluid which comprises a dissolved metal complex of a metal of transition group VIII of the Periodic Table of the Elements with at least one phosphoramidite compound as ligand, wherein the fluid is brought into contact with at least one base selected from trialkyl amines, dialkyaryl amines, alkyldiaryl amines, triaryl amines, and bases immobilized on a solid phase, or a combination thereof, and wherein the phosphoramidite compound is selected from among compounds of the formulae I and II

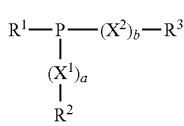  (I)

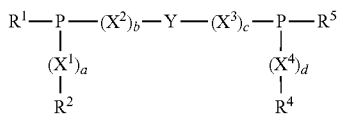  (II)

where

R¹ and R⁵ are each, independently of one another, pyrrole groups bound via the nitrogen atom to the phosphorus atom, R², R³ and R⁴ are each, independently of one another, alkyl, cycloalkyl, heterocycloalkyl, aryl or hetaryl, or R¹ together with R² and/or R⁴ together with R⁵ forms a divalent group containing at least one pyrrole group bound via the pyrrolic nitrogen atom to the phosphorus atom, Y is a divalent bridged group having from 2 to 20 bridge atoms between the flanking bonds, X¹, X², X³ and X⁴ are selected independently from among O, S, SiR$^\alpha$R$^\beta$ and NR$^\gamma$, where R$^\alpha$, R$^\beta$ and R$^\gamma$ are each, independently of one another, hydrogen, alkyl, cycloalkyl, heterocycloalkyl, aryl or hetaryl, and a, b, c and d are each, independently of one another, 0 or 1.

2. A process according to claim 1, further comprising removing from the reaction zone a product mixture which is subjected to a fractionation to give a fraction consisting essentially of a hydroformylation product and a fraction comprising the catalytically active fluid in which the by-products of the hydroformylation which have boiling points higher than that of the hydroformylation product are present and the metal complex is dissolved, and recirculating the catalytically active fluid to the reaction zone.

3. A process according to claim 1, wherein the at least one base is selected from bases soluble in the catalytically active fluid, bases immobilized on a solid phase or combinations thereof.

4. A process according to claim 1, wherein the base comprises a basic nitrogen.

5. A process according to claim 1, wherein the at least one base is soluble in the catalytic fluid and is present in a molar ratio of base to phosphoramidite compound of from 0.01:1 to 5:1, in the reaction zone.

6. A process according to claim 1, wherein the at least one base includes a base soluble in the catalytic fluid and a base immobilized on a solid phase and the immobilized base is capable of at least partly liberating the soluble base from acid-base adducts obtained by reaction of the soluble base with an acid.

7. A process according to claim 2, wherein the fractionation of the product mixture comprises a thermal separation step and at least one high-boiling soluble base remains in the catalytically active fluid after the fractionation.

8. A process according to claim 2, wherein at least one base immobilized on a solid phase is used and the catalytically active fluid obtained after fractionation is brought into contact with the immobilized base before it is recirculated to the reaction zone.

9. A process according to claim 1, wherein the phosphoramidite compound is selected from among compounds of the formula II.1

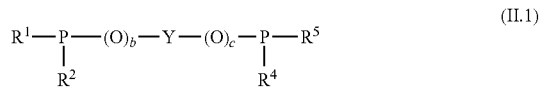  (II.1)

where R¹ and R⁵ are each, independently of one another, pyrrole groups bound via the nitrogen atom to the phosphorus atom, R² and R⁴ are each, independently of one another, alkyl, cycloalkyl, heterocycloalkyl, aryl or hetaryl, or R¹ together with R² and/or R⁴ together with R⁵ forms a divalent group containing at least one pyrrole group bound via the pyrrolic nitrogen atom to the phosphorus atom, Y is a divalent bridged group having from 2 to 20 bridge atoms between the flanking bonds, and b and c are each, independently of one another, 0 or 1.

10. A process according to claim 1, wherein R¹, R², R⁴ and R⁵ are selected independently from among groups of the formulae III.a to III.k

  (III.a)

  (III.b)

  (III.c)

  (III.d)

  (III.e)

  (III.f)

-continued
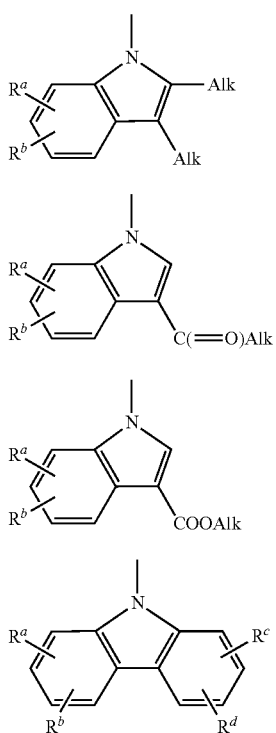
where
Alk is a $C_1$-$C_{12}$-alkyl group and
$R^a$, $R^b$, $R^c$ and $R^d$ are each, independently of one another, hydrogen, $C_1$-$C_4$-alkyl, $C_1$-$C_4$-alkoxy, acyl, halogen, $C_1$-$C_4$-alkoxycarbonyl or carboxyl.
11. A process according to claim 1, wherein the bridging group Y is selected from among groups of the formulae IV.a to IV.u
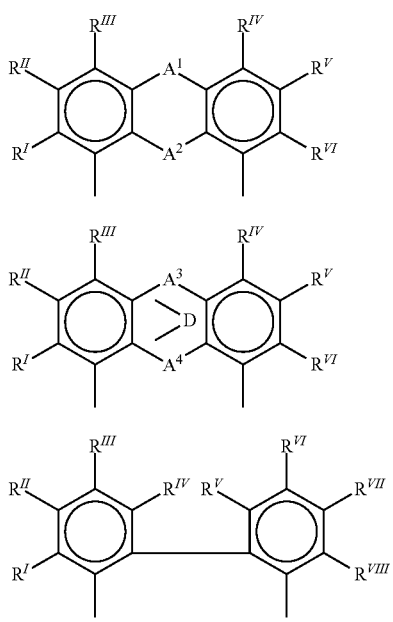
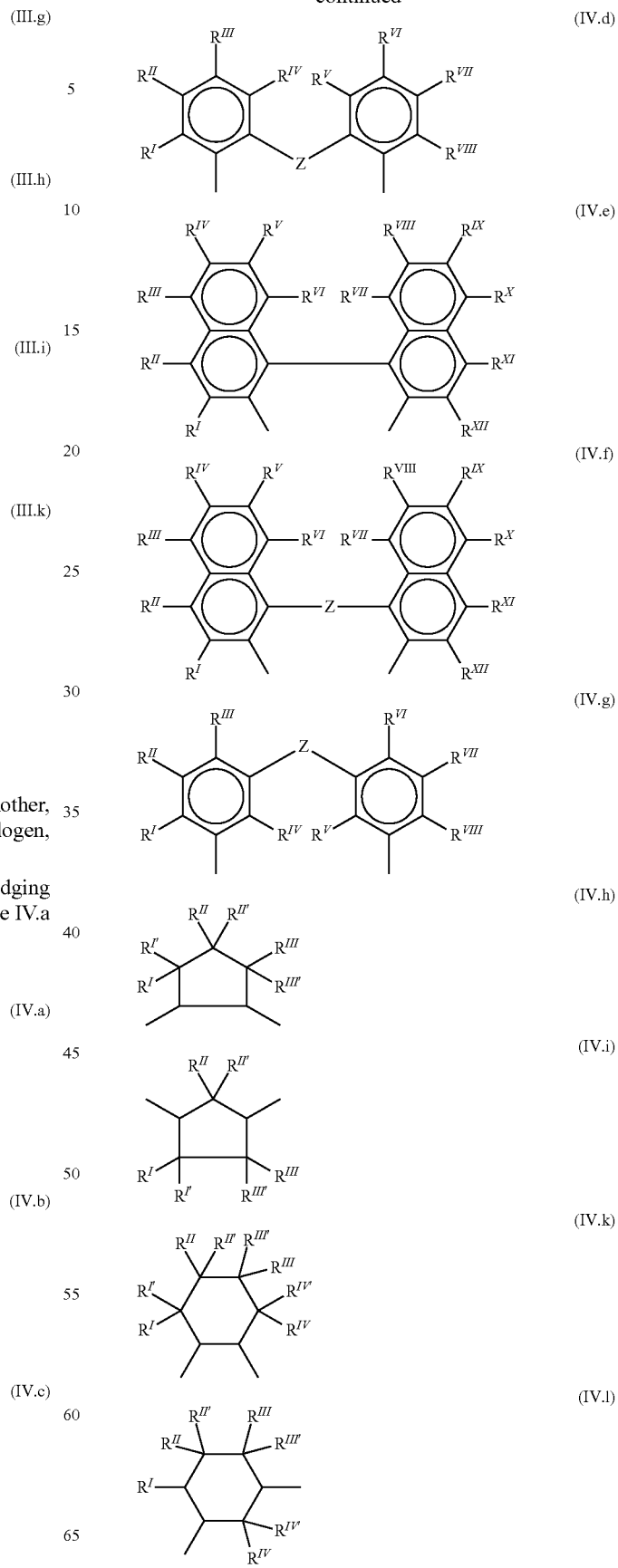

-continued

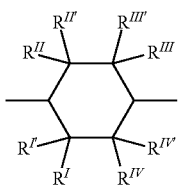
(IV.m)

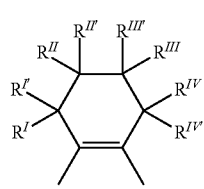
(IV.n)

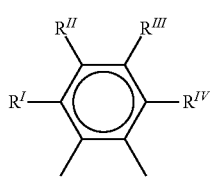
(IV.o)

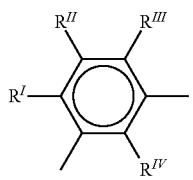
(IV.p)

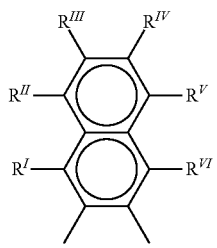
(IV.q)

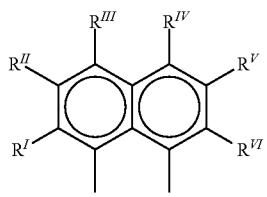
(IV.r)

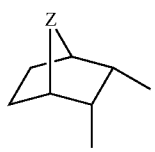
(IV.s)

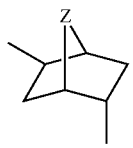
(IV.t)

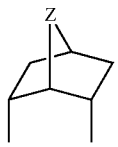
(IV.u)

where $R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$ and $R^{XII}$ are each independently of one another, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, where $E^1$ and $E^2$ are identical or different radicals selected from among hydrogen, alkyl, cycloalkyl and aryl, Z is O, S, $NR^\delta$ or $SiR^\delta R^\epsilon$, where $R^\delta$ and $R^\epsilon$ are each, independently of one another, hydrogen, alkyl, cycloalkyl, heterocycloalkyl, aryl or hetaryl, or Z is a $C_1$-$C_4$-alkylene bridge which may have a double bond and/or bear an alkyl, cycloalkyl, heterocycloalkyl, aryl or hetaryl substituent, or Z is a $C_1$-$C_4$-alkylene bridge which may have a double bond and/or bear an alkyl, cycloalkyl, heterocycloalkyl, aryl or hetaryl substituent, or Z is a $C_2$-$C_4$-alkylene bridge which is interrupted by O, S or $NR^\delta$ or $SiR^\delta R^\epsilon$, where, in the groups of the formulae IV.a and IV.b, two adjacent radicals $R^I$ to $R^{VI}$ together with the carbon atoms of the benzene ring to which they are bound may also form a fused ring system having 1, 2 or 3 further rings, where, in the groups of the formulae IV.h to IV.n, two geminal radicals $R^I$, $R^{I'}$; $R^{II}$, $R^{II'}$; $R^{III}$, $R^{III'}$ and/or $R^{IV}$, $R^{IV'}$ may also represent oxo or a ketal thereof, $A^1$ and $A^2$ are each, independently of one another, O, S, $SiR^\Phi R^\gamma$, $NR^\eta$ or $CR^\iota R^\kappa$, where $R^\Phi$, $R^\gamma$, $R^\eta$, $R^\iota$ and $R^\kappa$ are each, independently of one another, hydrogen, alkyl, cycloalkyl, heterocycloalkyl, aryl or hetaryl, $A^3$ and $A^4$ are each, independently of one another, SiR, N or $CR^\iota$, D is a divalent bridging group of the formula

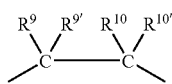

where $R^9$, $R^{9'}$, $R^{10}$ and $R^{10'}$ are each, independently of one another, hydrogen, alkyl, cycloalkyl, aryl, halogen, trifluoromethyl, carboxyl, carboxylate or cyano, where $R^{9'}$ together with $R^{10'}$ can also represent the second bond of a double bond between the two carbon atoms to which $R^{9'}$ and $R^{10'}$ are bound, and/or $R^9$ and $R^{10}$ together with the carbon atoms to which they are bound may also form a 4- to 8-membered carbocycle or heterocycle which may additionally be fused with one, two or three cycloalkyl, heterocycloalkyl, aryl or hetaryl groups, where the heterocycle and, if present, the fused-on groups may each bear, independently of one another, one, two, three or four substituents selected from among alkyl, cycloalkyl, heterocycloalkyl, aryl, hetaryl, $COOR^f$, $COO^-M^+$, $SO_3R^f$, $SO_3^-M^+$, $NE^4E^5$, alkylene- $NE^4E^5$, $NE^4E^5E^{6+}X^-$, alkylene-$NE^4E^5E^{6+}X^-$, $OR^f$, $SR^f$, $(CHR^eCH_2O)_yR^f$, $(CH_2N(E^4))_yR^f$, $(CH_2CH_2N(E^4))_yR^f$, halogen, trifluoromethyl, nitro, acyl and cyano, where $R^f$, $E^4$, $E^5$ and $E^6$ are identical or different radicals selected from among hydrogen, alkyl, cycloalkyl and aryl, $R^e$ is hydrogen, methyl or ethyl, $M^+$ is a cation, is an anion and y is an integer from 1 to 240.

12. A process according to claim 2 further comprising removing at least part of the by-products from the catalytically active fluid prior to recirculating the fluid.

13. A process according to claim 5, wherein the molar ratio is from 0.1:1 to 1.5:1.

14. A process according to claim 9, wherein $R^1$, $R^2$, $R^4$ and $R^5$ are selected independently from among groups of the formulae III.a to III.k (III.a)

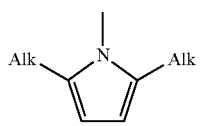

(III.b)

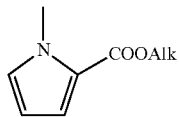

(III.c)

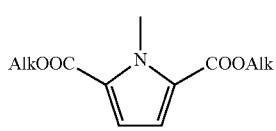

(III.d)

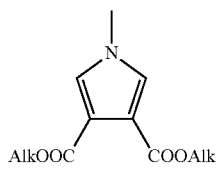

(III.e)

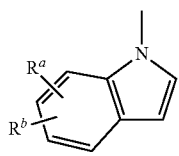

(III.f)

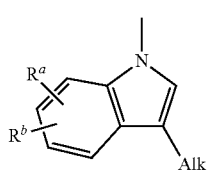

(III.g)

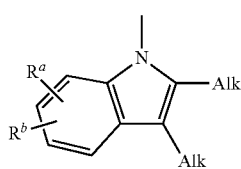

(III.h)

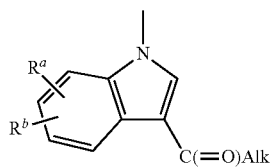

(III.i)

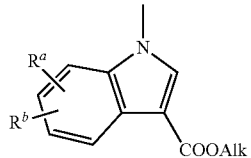

(III.k)

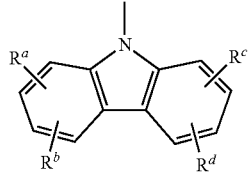

where

Alk is a $C_1$-$C_{12}$-alkyl group and $R^a$, $R^b$, $R^c$ and $R^d$ are each, independently of one another, hydrogen, $C_1$-$C_4$-alkyl, $C_1$-$C_4$-alkoxy, acyl, halogen, $C_1$-$C_4$-alkoxycarbonyl or carboxyl.

15. A process according to claim 9, wherein the bridging group Y is selected from among groups of the formulae IV.a to IV.u (IV.a)

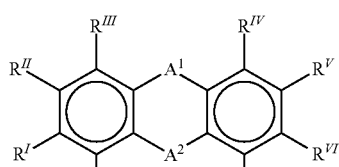

(IV.b)

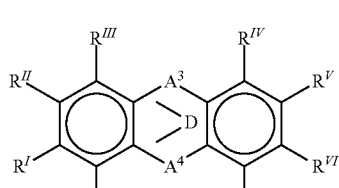

(IV.c)

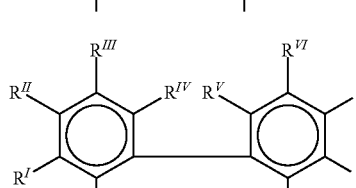

(IV.d)

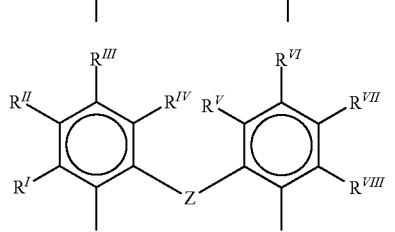

-continued
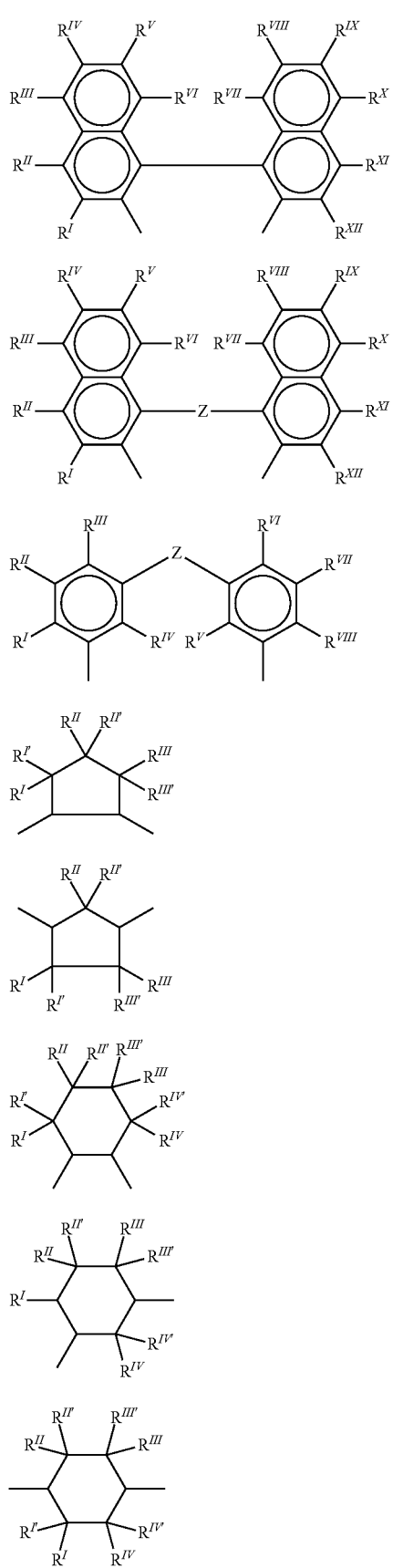
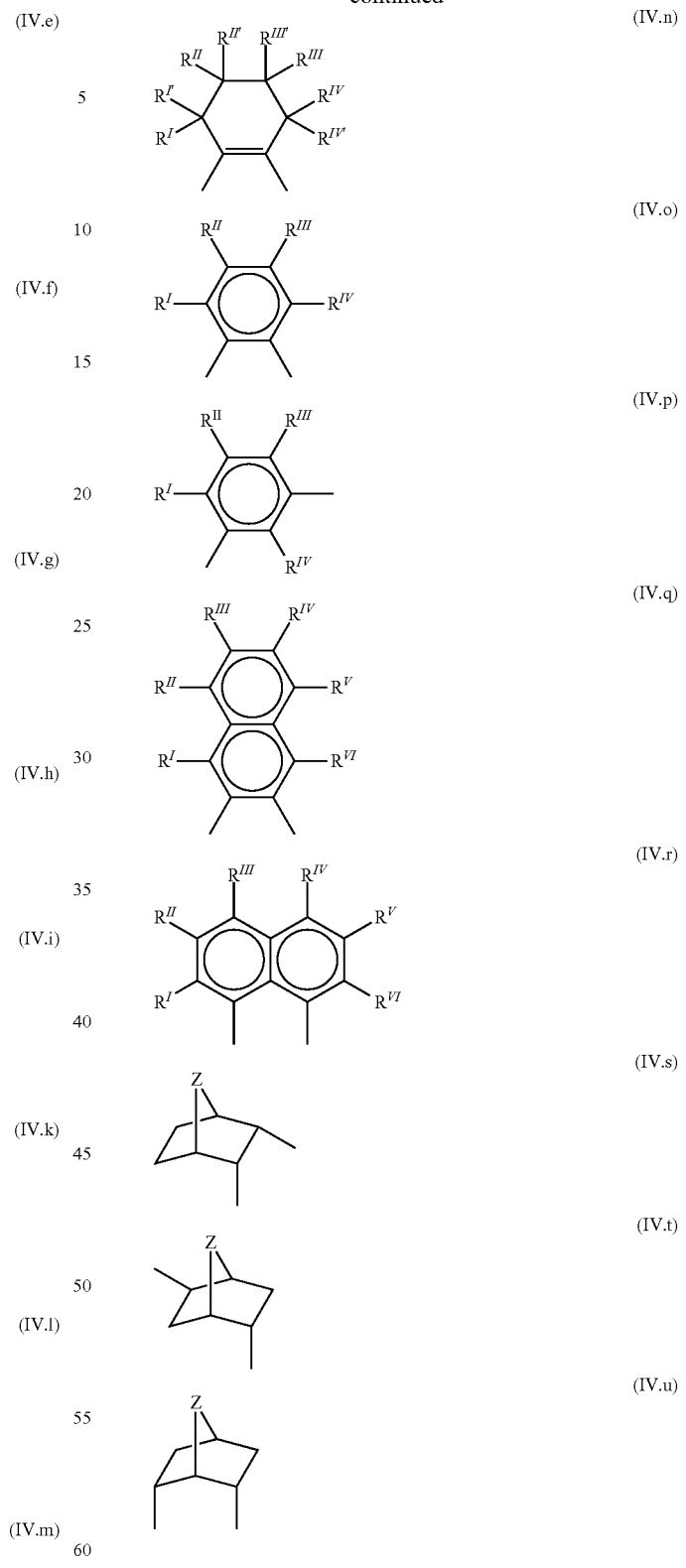
where
$R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$ and $R^{XII}$ are each, independently of one another, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, NE$^1$E$^2$, alkylene-NE$^1$E$^2$, nitro, alkoxycarbonyl, carboxyl, acyl or cyano, where E$^1$ and E$^2$ are identical or different radicals selected from among hydrogen, alkyl, cycloalkyl and aryl, Z is O, S, NR$^\delta$ or SiR$^\delta$R$^\epsilon$, where R$^\delta$ and R$^\epsilon$ are each, independently of one another, hydrogen, alkyl, cycloalkyl, heterocycloalkyl, aryl or hetaryl, or Z is a C$_1$-C$_4$-alkylene bridge which may have a double bond and/or bear an alkyl, cycloalkyl, heterocycloalkyl, aryl or hetaryl substituent, or Z is a C$_2$-C$_4$-alkylene bridge which is interrupted by O, S or NR$^\delta$ or SiR$^\delta$R$^\epsilon$, where, in the groups of the formulae IV.a and IV.b, two adjacent radicals R$^I$ to R$^{VI}$ together with the carbon atoms of the benzene ring to which they are bound may also form a fused ring system having 1, 2 or 3 further rings, where, in the groups of the formulae IV.h to IV.n, two geminal radicals R$^I$, R$^{I'}$; R$^{II}$, R$^{II'}$; R$^{III}$, R$^{III'}$ and/or R$^{IV}$, R$^{IV'}$ may also represent oxo or a ketal thereof, A$^1$ and A$^2$ are each, independently of one another, O, S, SiR$^\Phi$R$^\gamma$, NR$^\eta$ or CR$^\iota$R$^\kappa$, where R$^\Phi$, R$^\gamma$, R$^\eta$, R$^\iota$ and R$^\kappa$ are each, independently of one another, hydrogen, alkyl, cycloalkyl, heterocycloalkyl, aryl or hetaryl, A$^3$ and A$^4$ are each, independently of one another, SiR, N or CR$^\iota$, D is a divalent bridging group of the formula

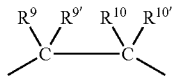

where

R$^9$, R$^{9'}$, R$^{10}$ and R$^{10'}$ are each, independently of one another, hydrogen, alkyl, cycloalkyl, aryl, halogen, trifluoromethyl, carboxyl, carboxylate or cyano, where R$^{9'}$ together with R$^{10'}$ can also represent the second bond of a double bond between the two carbon atoms to which R$^{9'}$ and R$^{10'}$ are bound, and/or R$^9$ and R$^{10}$ together with the carbon atoms to which they are bound may also form a 4- to 8-membered carbocycle or heterocycle which may additionally be ffsed with one, two or three cycloalkyl, heterocycloalkyl, aryl or hetaryl groups, where the heterocycle and, if present, the fused-on groups may each bear, independently of one another, one, two, three or four substituents selected from among alkyl, cycloalkyl, heterocycloalkyl, aryl, hetaryl, COOR$^f$, COO$^-$M$^+$, SO$_3$R$^f$, SO$^-_3$M$^+$, NE$^4$E$^5$, alkylene-NE$^4$E$^5$, NE$^4$E$^5$E$^{6+}$X$^-$, alkylene-NE$^4$E$^5$E$^{6+}$X$^-$, OR$^f$, SR$^f$, (CHR$^e$CH$_2$O)$_y$R$^f$, (CH$_2$N(E$^4$))$_y$R$^f$, (CH$_2$CH$_2$N(E$^4$))$_y$R$^f$, halogen, trifluoromethyl, nitro, acyl and cyano, where R$^f$, E$^4$, E$^5$ and E$^6$ are identical or different radicals selected from among hydrogen, alkyl, cycloalkyl and aryl, R$^e$ is hydrogen, methyl or ethyl, M$^+$ is a cation, is an anion and y is an integer from 1 to 240.

16. A process according to claim 10, wherein the bridging group Y is selected from among groups of the formulae IV.a to IV.u

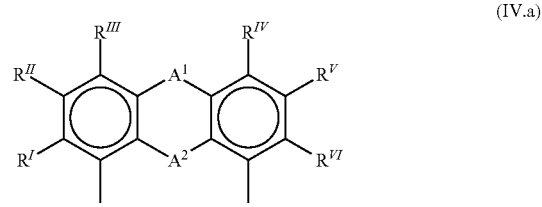

(IV.a)

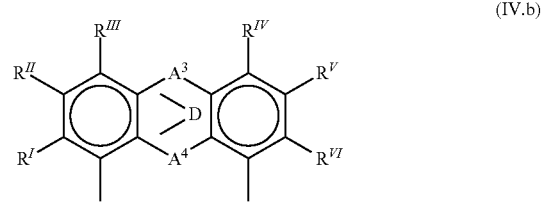

(IV.b)

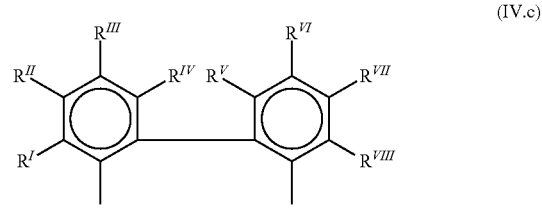

(IV.c)

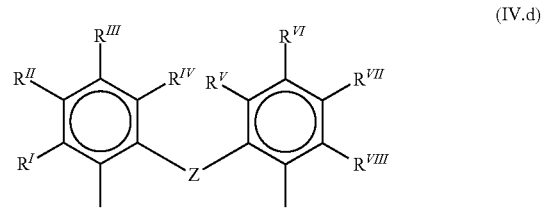

(IV.d)

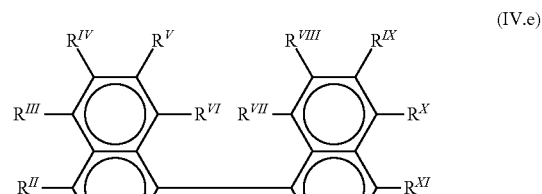

(IV.e)

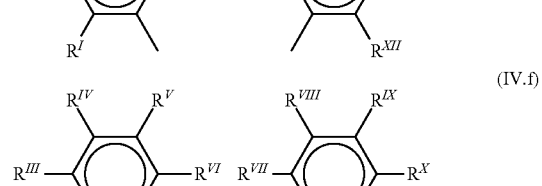

(IV.f)

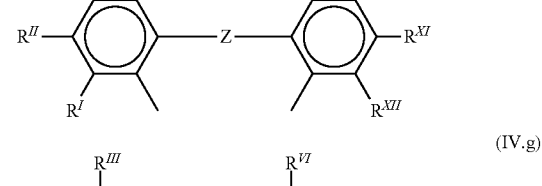

(IV.g)

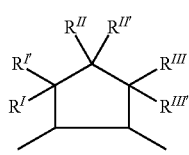
(IV.h)

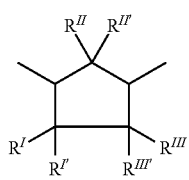
(IV.i)

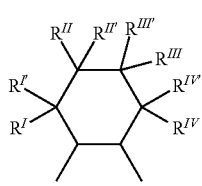
(IV.k)

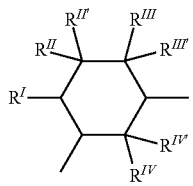
(IV.l)

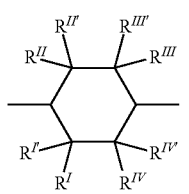
(IV.m)

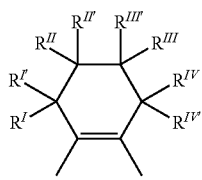
(IV.n)

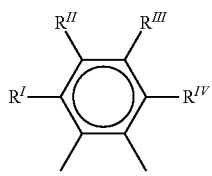
(IV.o)

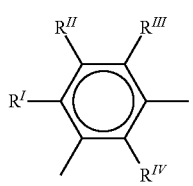
(IV.p)

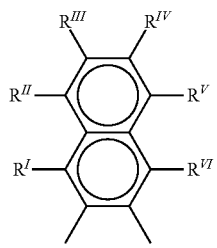
(IV.q)

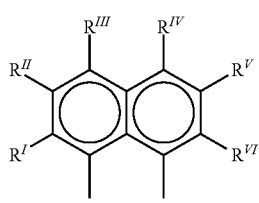
(IV.r)

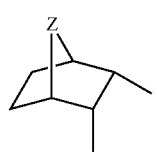
(IV.s)

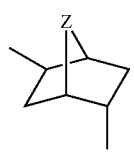
(IV.t)

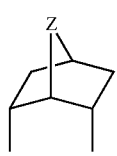
(IV.u)

where $R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$ and $R^{XII}$ are each, independently of one another, hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^1E^2$, alkylene-$NE^1E^2$, nitro, alkoxycarbonyl, carboxyl, acyl or cyano, where $E^1$ and $E^2$ are identical or different radicals selected from among hydrogen, alkyl, cycloalkyl and aryl, Z is O, S, $NR^\delta$ or $SiR^\delta R^\epsilon$, where $R^\delta$ and $R^\epsilon$ are each, independently of one another, hydrogen, alkyl, cycloalkyl, heterocycloalkyl, aryl or hetaryl, or Z is a $C_1$-$C_4$-alkylene bridge which may have a double bond and/or bear an alkyl, cycloalkyl, heterocycloalkyl, aryl or hetaryl substituent, or Z is a $C_2$-$C_4$-alkylene bridge which is interrupted by O, S or $NR^\delta$ or $SiR^\delta R^\epsilon$, where, in the groups of the formulae IV.a and IV.b, two adjacent radicals $R^I$ to $R^{VI}$ together with the carbon atoms of the benzene ring to which they are bound may also form a fused ring system having 1, 2 or 3 further rings, where, in the groups of the formulae IV.h to IV.n, two geminal radicals $R^I$, $R^{I'}$; $R^{II}$, $R^{II'}$; $R^{III}$, $R^{III'}$ and/or $R^{IV}$, $R^{IV'}$ may also represent oxo or a ketal thereof, $A^1$ and $A^2$ are each, independently of one another, O, S, $SiR^\phi R^\gamma$, $NR^\eta$ or $CR^\iota R^\kappa$, where $R^\phi$, $R^\gamma$, $R^\eta$, $R^\iota$ and $R^\kappa$ are each, independently of one another, hydrogen, alkyl, cycloalkyl, heterocycloalkyl, aryl or hetaryl, $A^3$ and $A^4$ are each, independently of one another, $SiR$, N or $CR^t$, D is a divalent bridging group of the formula

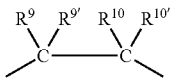

where $R^9$, $R^{9'}$, $R^{10}$ and $R^{10'}$ are each, independently of one another, hydrogen, alkyl, cycloalkyl, aryl, halogen, trifluoromethyl, carboxyl, carboxylate or cyano, where $R^{9'}$ together with $R^{10'}$ can also represent the second bond of a double bond between the two carbon atoms to which $R^{9'}$ and $R^{10'}$ are bound, and/or $R^9$ and $R^{10}$ together with the carbon atoms to which they are bound may also form a 4- to 8-membered carbocycle or heterocycle which may additionally be fused with one, two or three cycloalkyl, heterocycloalkyl, aryl or hetaryl groups, where the heterocycle and, if present, the fuised-on groups may each bear, independently of one another, one, two, three or four substituents selected from among alkyl, cycloalkyl, heterocycloalkyl, aryl, hetaryl, $COOR^f$, $COO^-M^+$, $SO_3R^f$, $SO^-_3M^+$, $NE^4E^5$, alkylene-$NE^4E^5$, $NE^4E^5E^{6+}X^-$, alkylene-$NE^4E^5E^{6+}X^-$, $OR^f$, $SR^f$, $(CHR^eCH_2O)_yR^f$, $(CH_2N(E^4))_yR^f$, $(CH_2CH_2N(E^4))_yR^f$, halogen, trifluoromethyl, nitro, acyl and cyano, where $R^f$, $E^4$, $E^5$ and $E^6$ are identical or different radicals selected from among hydrogen, alkyl, cycloalkyl and aryl, $R^e$ is hydrogen, methyl or ethyl, $M^+$ is a cation, is an anion and y is an integer from 1 to 240.

17. A process for the hydroformylation of compounds which comprises, providing at least one compound with an ethylenically unsaturated double bond and reacting the at least one compound with carbon monoxide and hydrogen in at least one reaction zone in the presence of a catalytically active fluid which comprises a dissolved metal complex of a metal of transition group VIII of the Periodic Table of the Elements with at least one phosphoramidite compound as ligand, wherein the fluid is brought into contact with at least one base selected from trialkyl amines, dialkyaryl amines, alkyldiaryl amines, and triaryl amines, and wherein the phosphoramidite compound is selected from among compounds of the formulae I and II

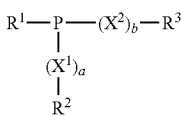

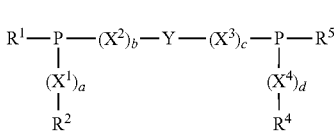

where $R^1$ and $R^5$ are each, independently of one another, pyrrole groups bound via the nitrogen atom to the phosphorus atom, $R^2$, $R^3$ and $R^4$ are each, independently of one another, alkyl, cycloalkyl, heterocycloalkyl, aryl or hetaryl, or $R^1$ together with $R^2$ and/or $R^4$ together with $R^5$ forms a divalent group containing at least one pyrrole group bound via the pyrrolic nitrogen atom to the phosphorus atom, Y is a divalent bridged group having from 2 to 20 bridge atoms between the flanking bonds, $X^1$, $X^2$, $X^3$ and $X^4$ are selected independently from among O, S, $SiR^\alpha R^\beta$ and $NR^\gamma$, where $R^\alpha$, $R^\beta$ and $R^\gamma$ are each, independently of one another, hydrogen, alkyl, cycloalkyl, heterocycloalkyl, aryl or hetaryl, and a, b, c and d are each, independently of one another, 0 or 1, further comprising removing from the reaction zone a product mixture which is subjected to a fractionation to give a fraction consisting essentially of a hydroformylation product and a fraction comprising the catalytically active fluid in which the by-products of the hydroformylation which have boiling points higher than that of the hydroformylation product are present and the metal complex is dissolved, and recirculating the catalytically active fluid to the reaction zone.

18. The process according to claim 17, wherein the recirculating of the catalytically active fluid is carried out in the absence of carbon monoxide and hydrogen.

19. A method of stabilizing a catalytically active fluid comprising a dissolved metal complex of a metal of transition group VIII of the Periodic Table of the Elements with at least one phosphoramidite compound as ligand in the hydroformylation of ethylenically unsaturated compounds, which comprises bringing the fluid into contact with at least one base selected from trialkyl amines, dialkyaryl amines, alkyldiaryl amines, triaryl amines, and bases immobilized on a solid phase, or a combination thereof, wherein the at least one phosphoramidite compound is selected from among compounds of the formulae I and II

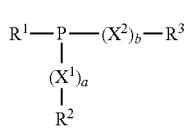

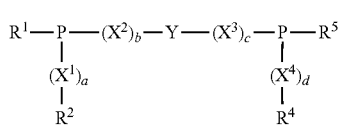

where $R^1$ and $R^5$ are each, independently of one another, pyrrole groups bound via the nitrogen atom to the phosphorus atom, $R^2$, $R^3$ and $R^4$ are each, independently of one another, alkyl, cycloalkyl, heterocycloalkyl, aryl or hetaryl, or $R^1$ together with $R^2$ and/or $R^4$ together with $R^5$ forms a divalent group containing at least one pyrrole group bound via the pyrrolic nitrogen atom to the phosphorus atom, Y is a divalent bridged group having from 2 to 20 bridge atoms between the flanking bonds, $X^1$, $X^2$, $X^3$ and $X^4$ are selected independently from among O, S, $SiR^\alpha R^\beta$ and $NR^\gamma$, where $R^\alpha$, $R^\beta$ and $R^\gamma$ are each, independently of one another, hydrogen, alkyl, cycloalkyl, heterocycloalkyl, aryl or hetaryl, and a, b, c and d are each, independently of one another, 0 or 1.

20. A method according to claim 19, wherein base is soluble in the catalytically active fluid and/or the fluid is brought into contact with a base immobilized on a solid phase.

* * * * *